US012669503B2

(12) United States Patent
Laing et al.

(10) Patent No.: US 12,669,503 B2
(45) Date of Patent: Jun. 30, 2026

(54) SYSTEMS AND METHODS FOR COMPREHENSIVE AND STANDARDIZED IMMUNE SYSTEM PHENOTYPING AND AUTOMATED CELL CLASSIFICATION

(71) Applicant: Melio Healthcare Limited, London (GB)

(72) Inventors: Adam Laing, London (GB); Thomas Hayday, London (GB); Jennie Yang, London (GB); Jeremy Mason, Cambridge (GB); Eduardo Alves, London (GB); Per Ullberg, Knivsta (SE)

(73) Assignee: Melio Healthcare Limited, London (GB)

( * ) Notice: Subject to any disclaimer, the term of this patent is extended or adjusted under 35 U.S.C. 154(b) by 573 days.

(21) Appl. No.: 18/353,022

(22) Filed: Jul. 14, 2023

(65) Prior Publication Data

US 2024/0192210 A1     Jun. 13, 2024

Related U.S. Application Data

(60) Provisional application No. 63/386,476, filed on Dec. 7, 2022.

(51) Int. Cl.
G16B 20/00 (2019.01)
G01N 33/569 (2006.01)

(52) U.S. Cl.
CPC ....... G01N 33/56972 (2013.01); G16B 20/00 (2019.02)

(58) Field of Classification Search
CPC .......................... G01N 33/56972; G16B 20/00
See application file for complete search history.

(56) References Cited

U.S. PATENT DOCUMENTS

| | | | |
|---|---|---|---|
| 2019/0263912 A1 | 8/2019 | Haber | |
| 2022/0317134 A1 * | 10/2022 | Patterson | A61K 45/06 |
| 2023/0245479 A1 * | 8/2023 | Zaitsev | G06N 5/01 |

FOREIGN PATENT DOCUMENTS

| | | | | |
|---|---|---|---|---|
| WO | WO-2020081582 A1 * | 4/2020 | | G06N 3/045 |
| WO | WO-2021193673 A1 * | 9/2021 | | G06N 20/20 |

OTHER PUBLICATIONS

Aghaeepour et al. (Mar. 2013). "Critical assessment of automated flow cytometry data analysis techniques," Nature Methods 10(3):228-238.

(Continued)

*Primary Examiner* — Stephen R Koziol
*Assistant Examiner* — Raven Simone Jones
(74) *Attorney, Agent, or Firm* — Morrison & Foerster LLP

(57)     ABSTRACT

Method and systems for generating an immune profile for a subject are described. In some instances, the methods comprise contacting at least a first aliquot of a sample from the subject with at least a first immunophenotyping panel to fluorescently-label cells contained within the sample; processing the fluorescently-labeled cells using a full spectrum flow cytometer to generate fluorescence intensity data, or data derived therefrom, for fluorescently-labeled cells from the sample; providing at least a subset of the fluorescence intensity data, or data derived therefrom, for the fluorescently-labeled cells as input to an ensemble machine learning model configured to process the data and classify individual cells as belonging to one of a plurality of distinct immune cell sub-populations; and outputting a total cell count or cell frequency for each of the plurality of distinct immune cell sub-populations in the sample as part of an immune profile for the subject.

30 Claims, 14 Drawing Sheets
(7 of 14 Drawing Sheet(s) Filed in Color)

100                            108

102        104        106        110        112

(56)  References Cited

OTHER PUBLICATIONS

Burton et al. (Jun. 2021). "CytoPy: An autonomous cytometry analysis framework," PLOS Computational Biology 17 (6):1-21.

Georas et al. (2005). "T-helper cell type-2 regulation in allergic disease," European Respiratory Journal 26 (6):1119-1137.

Lyons et al. (Aug. 2017). "Immune cell profiling in cancer: molecular approaches to cell-specific identification," npj Precision Oncology 26:1-8.

Mahnke et al. (Sep. 2012). "OMIP-013: Differentiation of Human T-Cells," Journal of the International Society for Advancement of Cytometry 81(11):935-936.

Verschoor et al. (Jul. 2015). "An introduction to automated flow cytometry gating tools and their implementation," Frontiers in Immunology 6(380):1-9.

Zambrano-Zaragoza et al. (Aug. 2014). "Th17 Cells in Autoimmune and Infectious Diseases," International Journal of Inflammation 2014:1-12.

Barrio et al. (2020). "optimalFlow: optimal transport approach to flow cytometry gating and population matching," BMC Bioinformatics 21(479):1-25.

International Search Report and Written Opinion mailed Oct. 23, 2023, directed to International Application No. PCT/EP2023/069629; 13 pages.

* cited by examiner

|  | precision | recall | f1-score | support |
|---|---|---|---|---|
| Eosinophil | 0.91 | 0.95 | 0.93 | 2856 |
| Neutrophil | 1.00 | 1.00 | 1.00 | 34649 |
| CD19p | 0.96 | 0.98 | 0.97 | 4147 |
| GDT | 0.88 | 0.64 | 0.75 | 1169 |
| CD4p_CD8p_T | 0.00 | 0.00 | 0.00 | 245 |
| Tconv | 0.95 | 0.98 | 0.96 | 11381 |
| Treg | 0.86 | 0.13 | 0.23 | 819 |
| CD8p_T | 0.97 | 0.95 | 0.96 | 11289 |
| DN_T | 0.69 | 0.15 | 0.25 | 1176 |
| CD14lo_CD16p_monocyte | 0.00 | 0.00 | 0.00 | 512 |
| CD14p_CD16n_monocyte | 0.91 | 0.95 | 0.93 | 4947 |
| CD14p_CD16p_monocyte | 0.00 | 0.00 | 0.00 | 34 |
| CD56bright_NK | 0.83 | 0.19 | 0.31 | 294 |
| CD56lo_CD16n_NK | 0.00 | 0.00 | 0.00 | 187 |
| CD56lo_CD16p_NK | 0.92 | 0.98 | 0.95 | 5407 |
| CD56p_CD16p_NK | 0.00 | 0.00 | 0.00 | 56 |
| unclassified | 0.77 | 0.42 | 0.55 | 3866 |
|  |  |  |  |  |
| micro avg | 0.96 | 0.92 | 0.94 | 83034 |
| macro avg | 0.63 | 0.49 | 0.52 | 83034 |
| weighted avg | 0.94 | 0.92 | 0.92 | 83034 |
| samples avg | 0.91 | 0.92 | 0.91 | 83034 |

FIG. 8

|  | precision | recall | f1-score | support |
|---|---|---|---|---|
| Eosinophil | 0.98 | 0.96 | 0.97 | 32857 |
| Neutrophil | 1.00 | 1.00 | 1.00 | 600498 |
| CD19p | 0.99 | 0.99 | 0.99 | 30234 |
| GDT | 0.98 | 0.96 | 0.97 | 13145 |
| CD4p_CD8p_T | 0.85 | 0.62 | 0.72 | 2058 |
| Tconv | 0.99 | 0.99 | 0.99 | 126457 |
| Treg | 0.97 | 0.95 | 0.96 | 8634 |
| CD8p_T | 0.99 | 0.98 | 0.98 | 71568 |
| DN_T | 0.88 | 0.85 | 0.86 | 9304 |
| CD14lo_CD16p_monocyte | 0.92 | 0.86 | 0.89 | 7323 |
| CD14p_CD16n_monocyte | 0.98 | 0.97 | 0.97 | 74074 |
| CD14p_CD16p_monocyte | 0.79 | 0.52 | 0.63 | 1105 |
| CD56bright_NK | 0.96 | 0.88 | 0.92 | 2962 |
| CD56lo_CD16n_NK | 0.72 | 0.35 | 0.47 | 2025 |
| CD56lo_CD16p_NK | 0.95 | 0.98 | 0.97 | 54604 |
| CD56p_CD16p_NK | 0.72 | 0.22 | 0.34 | 284 |
| unclassified | 0.90 | 0.88 | 0.89 | 46234 |
|  |  |  |  |  |
| micro avg | 0.98 | 0.98 | 0.98 | 1083366 |
| macro avg | 0.92 | 0.82 | 0.85 | 1083366 |
| weighted avg | 0.98 | 0.98 | 0.98 | 1083366 |
| samples avg | 0.98 | 0.98 | 0.98 | 1083366 |

FIG. 9

|  | precision | recall | f1-score | support |
|---|---|---|---|---|
| Eosinophil | 0.98 | 0.97 | 0.98 | 5613 |
| Neutrophil | 1.00 | 1.00 | 1.00 | 265253 |
| CD19p | 1.00 | 0.99 | 0.99 | 15790 |
| GDT | 0.96 | 0.99 | 0.98 | 16439 |
| CD4p_CD8p_T | 0.70 | 0.75 | 0.73 | 438 |
| Tconv | 0.99 | 0.98 | 0.98 | 51222 |
| Treg | 0.89 | 0.98 | 0.93 | 2504 |
| CD8p_T | 0.98 | 0.97 | 0.98 | 22539 |
| DN_T | 0.91 | 0.89 | 0.90 | 3033 |
| CD14lo_CD16p_monocyte | 0.99 | 0.56 | 0.71 | 2907 |
| CD14p_CD16n_monocyte | 0.95 | 0.99 | 0.97 | 25011 |
| CD14p_CD16p_monocyte | 0.40 | 0.22 | 0.28 | 254 |
| CD56bright_NK | 0.65 | 0.99 | 0.79 | 373 |
| CD56lo_CD16n_NK | 0.12 | 0.34 | 0.18 | 154 |
| CD56lo_CD16p_NK | 0.98 | 0.91 | 0.94 | 17788 |
| CD56p_CD16p_NK | 0.00 | 0.00 | 0.00 | 34 |
| unclassified | 0.91 | 0.85 | 0.88 | 14317 |
|  |  |  |  |  |
| micro avg | 0.99 | 0.98 | 0.98 | 443669 |
| macro avg | 0.79 | 0.79 | 0.78 | 443669 |
| weighted avg | 0.99 | 0.98 | 0.98 | 443669 |
| samples avg | 0.98 | 0.98 | 0.98 | 443669 |

FIG. 10

|  | precision | recall | f1-score | support |
|---|---|---|---|---|
| Eosinophil | 1.00 | 0.96 | 0.98 | 37404 |
| Neutrophil | 1.00 | 1.00 | 1.00 | 127227 |
| CD19p | 0.99 | 0.95 | 0.97 | 5598 |
| GDT | 0.99 | 0.96 | 0.98 | 5051 |
| CD4p_CD8p_T | 0.92 | 0.39 | 0.55 | 807 |
| Tconv | 0.97 | 1.00 | 0.98 | 31754 |
| Treg | 0.93 | 0.96 | 0.94 | 1998 |
| CD8p_T | 0.99 | 0.96 | 0.97 | 38204 |
| DN_T | 0.45 | 0.74 | 0.56 | 1450 |
| CD14lo_CD16p_monocyte | 0.65 | 0.56 | 0.60 | 461 |
| CD14p_CD16n_monocyte | 0.91 | 0.99 | 0.95 | 16549 |
| CD14p_CD16p_monocyte | 0.70 | 0.17 | 0.27 | 112 |
| CD56bright_NK | 0.57 | 0.97 | 0.72 | 396 |
| CD56lo_CD16n_NK | 0.99 | 0.19 | 0.32 | 26498 |
| CD56lo_CD16p_NK | 0.02 | 0.88 | 0.03 | 386 |
| CD56p_CD16p_NK | 0.20 | 0.33 | 0.25 | 3 |
| unclassified | 0.92 | 0.90 | 0.91 | 28863 |
|  |  |  |  |  |
| micro avg | 0.91 | 0.91 | 0.91 | 322761 |
| macro avg | 0.78 | 0.76 | 0.71 | 322761 |
| weighted avg | 0.98 | 0.91 | 0.92 | 322761 |
| samples avg | 0.91 | 0.91 | 0.91 | 322761 |

FIG. 11

SYSTEMS AND METHODS FOR COMPREHENSIVE AND STANDARDIZED IMMUNE SYSTEM PHENOTYPING AND AUTOMATED CELL CLASSIFICATION

CROSS-REFERENCE TO RELATED APPLICATIONS

This application claims the priority benefit of U.S. Provisional Application No. 63/386,476, filed Dec. 7, 2022, the contents of which are incorporated herein by reference in their entirety.

FIELD

This disclosure is related to methods and systems for the generation of standardized and comprehensive immune profiles for mammalian (e.g., human) subjects.

BACKGROUND

Immune profiling, i.e., the analysis of a subject's immune health at the serological or cellular level at a given point in time, can aid in diagnosing immune-related diseases and disorders (e.g., allergies, overreactive immune responses (as in asthma and Crohn's disease (inflammatory bowel disease)), or autoimmune diseases (such as autoimmune polyglandular syndrome and some facets of diabetes; see, for example, "Diseases of the Immune System", National Center for Biotechnology Information (US), in "Genes and Disease" [Internet], 1998, Bethesda (MD)). Immune profiling can also be used to, e.g., identify an individual's specific response to infectious diseases (e.g., viral, bacterial, fungal, or parasite infections), to monitor the response of patients, e.g., cancer patients, to treatment (see, e.g., Lyons, et al. (2017), "Immune Cell Profiling in Cancer: Molecular Approaches to Cell-Specific Identification", Precision Oncology 1, 26), and potentially, to predict healthcare outcomes.

Conventional methods for generating an immune profile include, e.g., enzyme-linked immunosorbent assays (ELISAs), immunoblotting techniques, and flow cytometry-based techniques comprising the use of panels of fluorescently-labeled antibodies directed to a variety of cell surface receptors and manual gating of the flow cytometry data. However these techniques are often laborious and time-consuming, and are not easily scalable to a level that enables the processing of hundreds or thousands of sample.

More recently, automated techniques have been applied to flow cytometry-based methods. Several programmatic approaches exist to finding high dimensional clusters of labeled immune cells and identifying them accordingly using manual expert guidance. Off-the-shelf clustering algorithms are often used for this purpose, including tSNE, FlowSOM, UMAP, etc. Other purpose-built algorithms also exist for defining labeled cell clusters in high-dimensional immunespace, e.g., flowType and Phenograph. Additionally, companies like Cytapex and Dotmatics OMIQ produce automated cell gating using similar methods. However, despite the existence of established immune profiling platforms and approaches, the immunophenotyping panels used in various experiments tend to differ, requiring a user to configure existing automated gating methods on a per-experiment basis. As a result, direct comparability between experiments is reduced or eliminated. Hence there is a need for improved methods and systems that are capable of providing standardized and comprehensive immune profiles for subjects of interest (e.g., patients) that will facilitate biomedical research and enable improved healthcare outcomes.

BRIEF SUMMARY

Disclosed herein are methods and systems for processing a sample, such as a blood sample, and generating a standardized and comprehensive immune profile for the subject. The disclosed methods and systems combine full spectrum flow cytometry (FSFC)-based analysis of cells within the sample with an ensemble machine learning-based approach to filtering and classifying individual immune cells into a plurality of distinct immune cell sub-populations. The key advantages of the disclosed methods and systems are enabled by standardizing the immune profiling platform (including the immunophenotyping panels used for fluorescently-labeling cells) and implementing automated data processing. This in turn enables the processing of highly complex FSFC data to generate translatable immune profiles in clinically-relevant timeframes (i.e., hours).

Disclosed herein are methods for generating an immune profile for a subject, the methods comprising: contacting at least a first aliquot of a sample from the subject with at least a first immunophenotyping panel to fluorescently-label cells contained within the sample; processing the fluorescently-labeled cells using a full spectrum flow cytometer to generate fluorescence intensity data, or data derived therefrom, for a plurality of fluorescently-labeled cells from the sample; providing at least a subset of the fluorescence intensity data, or data derived therefrom, for the plurality of fluorescently-labeled cells as input to an ensemble machine learning model configured to process the fluorescence intensity data, or data derived therefrom, and classify individual cells of the plurality of fluorescently-labeled cells as belonging to one of a plurality of distinct immune cell sub-populations; and outputting a total cell count or cell frequency for each of the plurality of distinct immune cell sub-populations in the sample as part of an immune profile for the subject.

In some embodiments, the ensemble machine learning model is organized in a cascading hierarchical tree structure comprising a plurality of nodes, and wherein each node comprises an individual machine learning model. In some embodiments, each individual machine learning model comprises one input data set and from one to eight output data sets corresponding to branches of the cascading hierarchical tree structure. In some embodiments, each individual machine learning model comprises a neural network model. In some embodiments, each individual machine learning model comprises a gradient descent boosted tree model. In some embodiments, the plurality of nodes comprises at least 1000, 1200, 1400, 1600, 1800, 2000, 2200, or 2400 nodes. In some embodiments, a number of individual machine learning models in the ensemble machine learning model is equal to a number of distinct immune cell sub-populations in the plurality of distinct immune cell sub-populations. In some embodiments, the design of the cascading hierarchical tree structure is based at least in part on an expert analysis of manually-gated fluorescence intensity data, or data derived therefrom, for one or more control samples.

In some embodiments, individual cells are classified independently of all other cells in the plurality of fluorescently-labeled cells. In some embodiments, individual cells are classified recursively with all other cells of the plurality of fluorescently-labeled cells.

In some embodiments, the ensemble machine learning model is trained using one or more labeled training data sets generated by an expert through manual gating of fluorescence intensity data, or data derived therefrom, for one or more control samples. In some embodiments, the individual machine learning models in the ensemble machine learning model are trained individually using the one or more labeled training data sets. In some embodiments, during training, an individual model's predictions are used to validate the individual model but do not propagate forward through the ensemble machine learning model, thereby eliminating error propagation during training. In some embodiments, the individual machine learning models in the ensemble machine learning model are trained collectively using a recursive training method. In some embodiments, the training of the ensemble machine learning model is controlled by one or more hyperparameter values that are the same for every node in the cascading hierarchical tree structure. In some embodiments, the training of the ensemble machine learning model is controlled by one or more hyperparameter values that are different for a subset of nodes in the cascading hierarchical tree structure. In some embodiments, the training of the ensemble machine learning model is controlled by one or more hyperparameter values that are determined by performing a random grid search of the value ranges for the one or more hyperparameters.

In some embodiments, the method further comprises performing a mathematical transformation of the fluorescence intensity data, or data derived therefrom, prior to using the transformed fluorescence intensity data as input for the ensemble machine learning model.

In some embodiments, the fluorescence intensity data, or data derived therefrom, comprises fluorescence intensity data for at least 2, 3, 4, 5, 6, 7, 8, 9, 10, 11, 12, 13, 14, 15, 20, 25, 30, 35, or 40 fluorescence detection channels. In some embodiments, the fluorescence intensity data, or data derived therefrom, further comprises forward scatter height data, forward scatter area data, side scatter height data, side scatter area data, autofluorescence data, or any combination thereof.

In some embodiments, the sample comprises a blood sample, a buffy coat sample, or a cell suspension.

In some embodiments, the at least one immunophenotyping panel comprises a panel of fluorescently-labeled antibodies directed to cell surface proteins associated with antigen-presenting cells (APCs). In some embodiments, the panel of fluorescently-labeled antibodies comprises fluorescently-labeled antibodies directed to IGM, CD5, CD62L, CD294, CD69, CD38, PD1, CD11C, CD3, CD8, HLADR, CD24, CD337, CD123, CD141, CD1C, CD4, TACI, CD319, CD335, PDL1, CD10, CD45, CD16, IGD, CD40, CD19_TCRGD, CD43, CD14, CD138, CD15, CD56, CD86, CD303, CD27, or any combination thereof. In some embodiments, the panel of fluorescently-labeled antibodies further comprises fluorescently-labeled antibodies directed to cell surface markers that are indicative of live cells, dead cells, or both.

In some embodiments, the at least one immunophenotyping panel comprises a panel of fluorescently-labeled antibodies directed to cell surface proteins associated with T cells. In some embodiments, the panel of fluorescently-labeled antibodies comprises fluorescently-labeled antibodies directed to TIGIT, CD5, CD28, CXCR5, CD39, TIM3, CD38, PD1, TCRVA7_2_TCRVD1, CD95, CD3, CD8, HLADR, CD31, CCR4, CCR6, CCR7, CD57, ICOS, CD4, KLRG1, TCRVA24_JA18, CD122, CD103, CXCR3, TCRVD2, CD45, CCR10, CD16, CD25, CD161, CD19_TCRGD, LAG3, CD14, CD45RO, CD56, CD127, CD45RA, CD27, or any combination thereof.

In some embodiments, the plurality of distinct immune cell sub-populations comprises at least 1000, 1200, 1400, 1600, 1800, 2000, 2200, or 2400 distinct immune cell sub-populations. In some embodiments, the plurality of distinct immune cell sub-populations includes white blood cells (WBC), Eosinophils, Eosinophil/CD5+, Neutrophils, Neutrophils/big, Neutrophils/CD5+, Neutrophils/small, B-cells, B-cells/CD5− CD27−, Monocytes/CD56+, Monocytes/CD56−, NK-cells, Dendritic cells (DC), T-cells, iNKT cells, gamma delta T-cells (total GD), Vd1 cells, Vd2 cells, Vdx cells, Mucosal-associated invariant T (MAIT) cells, TEMRA cells, CD4 naïve cells, T helper cells, CD4 effector memory cells, Treg cells, or any combination thereof.

In some embodiments, the total cell count or cell frequency for each of the plurality of distinct immune cell sub-populations in the sample is output as part of an immune profile in less than 24 hours, 12 hours, 10 hours, 8 hours, 6 hours, or 4 hours.

In some embodiments, the immune profile is used to diagnose an immune-related disease or disorder, monitor progression of an immune-related disease or disorder, or monitor a response to treatment of an immune-related disease or disorder in the subject.

Disclosed herein are computer-implemented methods for generating an immune profile for a subject, the methods comprising: receiving fluorescence intensity data, or data derived therefrom, generated using a full spectrum flow cytometer to process a fluorescently-labeled cell sample collected from the subject; providing at least a subset of the fluorescence intensity data, or data derived therefrom, for a plurality of fluorescently-labeled cells as input to an ensemble machine learning model configured to process the fluorescence intensity data, or data derived therefrom, and classify individual cells of the plurality of fluorescently-labeled cells as belonging to one of a plurality of distinct immune cell sub-populations; and outputting a total cell count or cell frequency for each of the plurality of distinct immune cell sub-populations in the sample as part of an immune profile for the subject.

In some embodiments, the ensemble machine learning model is organized in a cascading hierarchical tree structure comprising a plurality of nodes, and wherein each node comprises an individual machine learning model. In some embodiments, each individual machine learning model comprises one input data set and from one to eight output data sets corresponding to branches of the cascading hierarchical tree structure. In some embodiments, each individual machine learning model comprises a neural network model. In some embodiments, each individual machine learning model comprises a gradient descent boosted tree model. In some embodiments, the plurality of nodes comprises at least 1000, 1200, 1400, 1600, 1800, 2000, 2200, or 2400 nodes. In some embodiments, a number of individual machine learning models in the ensemble machine learning model is equal to a number of distinct immune cell sub-populations in the plurality of distinct immune cell sub-populations. In some embodiments, the design of the cascading hierarchical tree structure is based at least in part on an expert analysis of manually-gated fluorescence intensity data, or data derived therefrom, for one or more control samples.

In some embodiments, individual cells are classified independently of all other cells in the plurality of fluorescently-labeled cells. In some embodiments, individual cells are classified recursively with all other cells of the plurality of fluorescently-labeled cells.

In some embodiments, the ensemble machine learning model is trained using one or more labeled training data sets generated by an expert through manual gating of fluorescence intensity data, or data derived therefrom, for one or more control samples. In some embodiments, the individual machine learning models in the ensemble machine learning model are trained individually using the one or more labeled training data sets. In some embodiments, during training, an individual model's predictions are used to validate the individual model but do not propagate forward through the ensemble machine learning model, thereby eliminating error propagation during training. In some embodiments, the individual machine learning models in the ensemble machine learning model are trained collectively using a recursive training method. In some embodiments, the training of the ensemble machine learning model is controlled by one or more hyperparameter values that are the same for every node in the cascading hierarchical tree structure. In some embodiments, the training of the ensemble machine learning model is controlled by one or more hyperparameter values that are different for a subset of nodes in the cascading hierarchical tree structure. In some embodiments, the training of the ensemble machine learning model is controlled by one or more hyperparameter values that are determined by performing a random grid search of the value ranges for the one or more hyperparameters.

In some embodiments, the method further comprises performing a mathematical transformation of the fluorescence intensity data, or data derived therefrom, prior to using the transformed fluorescence intensity data as input for the ensemble machine learning model.

In some embodiments, the fluorescence intensity data, or data derived therefrom, comprises fluorescence intensity data for at least 2, 3, 4, 5, 6, 7, 8, 9, 10, 11, 12, 13, 14, 15, 20, 25, 30, 35, or 40 fluorescence detection channels. In some embodiments, the fluorescence intensity data, or data derived therefrom, further comprises forward scatter height data, forward scatter area data, side scatter height data, side scatter area data, autofluorescence data, or any combination thereof.

In some embodiments, the plurality of distinct immune cell sub-populations comprises at least 1000, 1200, 1400, 1600, 1800, 2000, 2200, or 2400 distinct immune cell sub-populations. In some embodiments, the plurality of distinct immune cell sub-populations includes white blood cells (WBC), Eosinophils, Eosinophil/CD5+, Neutrophils, Neutrophils/big, Neutrophils/CD5+, Neutrophils/small, B-cells, B-cells/CD5− CD27−, Monocytes/CD56+, Monocytes/CD56−, NK-cells, Dendritic cells (DC), T-cells, iNKT cells, gamma delta T-cells (total GD), Vd1 cells, Vd2 cells, Vdx cells, Mucosal-associated invariant T (MAIT) cells, TEMRA cells, CD4 naïve cells, T helper cells, CD4 effector memory cells, Treg cells, or any combination thereof.

In some embodiments, the total cell count or cell frequency for each of the plurality of distinct immune cell sub-populations in the sample is output as part of an immune profile in less than 24 hours, 12 hours, 10 hours, 8 hours, 6 hours, or 4 hours.

In some embodiments, the immune profile is used to diagnose an immune-related disease or disorder, monitor progression of an immune-related disease or disorder, or monitor a response to treatment of an immune-related disease or disorder in the subject.

Disclosed herein are systems comprising: one or more processors; and a memory communicatively coupled to the one or more processors and configured to store instructions that, when executed by the one or more processors, cause the system to: receive fluorescence intensity data, or data derived therefrom, generated using a full spectrum flow cytometer to process a fluorescently-labeled cell sample collected from a subject; provide at least a subset of the fluorescence intensity data, or data derived therefrom, for a plurality of fluorescently-labeled cells as input to an ensemble machine learning model configured to process the fluorescence intensity data, or data derived therefrom, and classify individual cells of the plurality of fluorescently-labeled cells as belonging to one of a plurality of distinct immune cell sub-populations; and output a total cell count or cell frequency for each of the plurality of distinct immune cell sub-populations in the sample as part of an immune profile for the subject. In some embodiments, the system further comprises a full spectrum flow cytometer.

Disclosed herein are non-transitory computer-readable storage media storing one or more programs, the one or more programs comprising instructions, which when executed by one or more processors of a system, cause the system to: receive fluorescence intensity data, or data derived therefrom, generated using a full spectrum flow cytometer to process a fluorescently-labeled cell sample collected from a subject; provide at least a subset of the fluorescence intensity data, or data derived therefrom, for a plurality of fluorescently-labeled cells as input to an ensemble machine learning model configured to process the fluorescence intensity data, or data derived therefrom, and classify individual cells of the plurality of fluorescently-labeled cells as belonging to one of a plurality of distinct immune cell sub-populations; and output a total cell count or cell frequency for each of the plurality of distinct immune cell sub-populations in the sample as part of an immune profile for the subject.

INCORPORATION BY REFERENCE

All publications, patents, and patent applications mentioned in this specification are herein incorporated by reference in their entirety to the same extent as if each individual publication, patent, or patent application was specifically and individually indicated to be incorporated by reference in its entirety. In the event of a conflict between a term herein and a term in an incorporated reference, the term herein controls.

BRIEF DESCRIPTION OF THE FIGURES

The patent or application file contains at least one drawing executed in color. Copies of this patent or patent application publication with color drawing(s) will be provided by the Office upon request and payment of the necessary fee.

Various aspects of the disclosed methods, devices, and systems are set forth with particularity in the appended claims. A better understanding of the features and advantages of the disclosed methods, devices, and systems will be obtained by reference to the following detailed description of illustrative embodiments and the accompanying drawings, of which:

FIG. 8 provides a non-limiting example of test data generated by a trained neural network classifier.

FIG. 9 provides another non-limiting example of test data generated by a trained neural network classifier.

FIG. 10 provides a non-limiting example of validation data generated by a trained neural network classifier.

FIG. 11 provides another non-limiting example of validation data generated by a trained neural network classifier.

DETAILED DESCRIPTION

Figure 1:
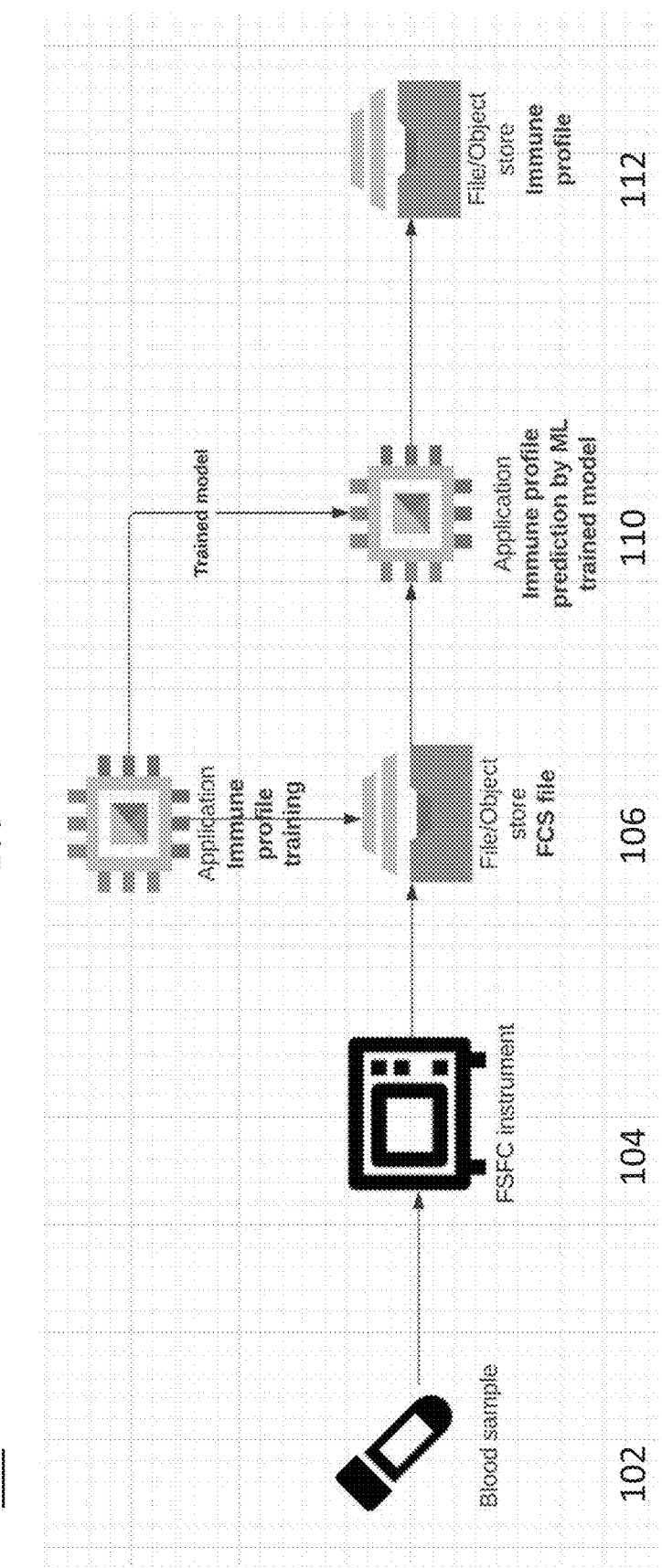
FIG. 1 provides a non-limiting example of a process flow diagram for a method of processing blood sample and generating an immune profile, according to one embodiment as described herein.

Disclosed herein are methods and systems for processing a sample, such as a blood sample, and generating a standardized and comprehensive immune profile for the subject. The disclosed methods and systems combine full spectrum flow cytometry (FSFC)-based analysis of cells within the sample with an ensemble machine learning-based approach to filtering and classifying individual immune cells into a plurality of distinct immune cell sub-populations. The key advantages of the disclosed methods and systems are enabled by standardizing the immune profiling platform (including the immunophenotyping panels used for fluorescently-labeling cells) and implementing automated data processing. This in turn enables the processing of highly complex FSFC data to generate translatable immune profiles in clinically-relevant timeframes (i.e., hours).

In some instances, for example, methods for generating an immune profile for a subject are described, the methods comprising: contacting at least a first aliquot of a sample from the subject with at least a first immunophenotyping panel to fluorescently-label cells contained within the sample; processing the fluorescently-labeled cells using a full spectrum flow cytometer to generate fluorescence intensity data, or data derived therefrom, for a plurality of fluorescently-labeled cells from the sample; providing at least a subset of the fluorescence intensity data, or data derived therefrom, for the plurality of fluorescently-labeled cells as input to an ensemble machine learning model configured to process the fluorescence intensity data, or data derived therefrom, and classify individual cells of the plurality of fluorescently-labeled cells as belonging to one of a plurality of distinct immune cell sub-populations; and outputting a total cell count or cell frequency for each of the plurality of distinct immune cell sub-populations in the sample as part of an immune profile for the subject.

Also described are systems comprising: one or more processors; and a memory communicatively coupled to the one or more processors and configured to store instructions that, when executed by the one or more processors, cause the system to: receive fluorescence intensity data, or data derived therefrom, acquired using a full spectrum flow cytometer to process a fluorescently-labeled cell sample collected from a subject; provide at least a subset of the fluorescence intensity data, or data derived therefrom, for the plurality of fluorescently-labeled cells as input to an ensemble machine learning model configured to process the fluorescence intensity data, or data derived therefrom, and classify individual cells of the plurality of fluorescently-labeled cells as belonging to one of a plurality of distinct immune cell sub-populations; and output a total cell count or cell frequency for each of the plurality of distinct immune cell sub-populations in the sample as part of an immune profile for the subject.

Also described are non-transitory computer-readable storage media storing one or more programs, the one or more programs comprising instructions, which when executed by one or more processors of a system, cause the system to: receive fluorescence intensity data, or data derived therefrom, acquired using a full spectrum flow cytometer to process a fluorescently-labeled cell sample collected from a subject; provide at least a subset of the fluorescence intensity data, or data derived therefrom, for the plurality of fluorescently-labeled cells as input to an ensemble machine learning model configured to process the fluorescence intensity data, or data derived therefrom, and classify individual cells of the plurality of fluorescently-labeled cells as belonging to one of a plurality of distinct immune cell sub-populations; and output a total cell count or cell frequency for each of the plurality of distinct immune cell sub-populations in the sample as part of an immune profile for the subject.

Definitions

Unless otherwise defined, all of the technical terms used herein have the same meaning as commonly understood by one of ordinary skill in the art in the field to which this disclosure belongs.

As used in this specification and the appended claims, the singular forms "a", "an", and "the" include plural references unless the context clearly indicates otherwise. Any reference to "or" herein is intended to encompass "and/or" unless otherwise stated, and encompasses any and all possible combinations of one or more of the associated listed items.

As used herein, the terms "includes, "including," "comprises," and/or "comprising" specify the presence of stated features, integers, steps, operations, elements, components, and/or units but do not preclude the presence or addition of one or more other features, integers, steps, operations, elements, components, units, and/or groups thereof.

Throughout this application, various parameter values may be presented in a range format. It should be understood that the description in range format is merely for convenience and brevity, and should not be construed as an inflexible limitation on the scope of the disclosure. Accordingly, the description of a range should be considered to have specifically disclosed all possible subranges as well as individual numerical values within that range, irrespective of whether a specific numerical value or specific sub-range is expressly stated. For example, description of a range such as from 1 to 6 should be considered to have specifically disclosed subranges such as from 1 to 3, from 1 to 4, from 1 to 5, from 2 to 4, from 2 to 6, from 3 to 6, etc., as well as individual numbers within that range, for example, 1, 1.4, 2, 3, 3.6, 4, 5, 5.8, and 6. This applies regardless of the breadth of the range.

Numbers may be expressed herein as being "about" a particular value. Similarly, ranges may be expressed herein as from "about" one particular value and/or to "about" another particular value. The terms "about" and "approximately" shall generally mean an acceptable degree of error or variation for a given value or range of values, such as, for example, a degree of error or variation that is within 20 percent (%), within 15%, within 10%, or within 5% of a given value or range of values.

It should be recognized that use of ordinal terms such as "first" and "second" in the description of methods and systems disclosed herein does not by itself connote any priority, order of importance of one system component over another, or the temporal order in which acts of a method are performed, but are used merely as labels to distinguish, for example, one system component having a certain name from another system component having the same name but for the use of the ordinal term to distinguish the two system components.

Additionally, various implementations of the methods and systems set forth herein may be described in terms of exemplary block diagrams, process flow charts, and other illustrations. As will become apparent to one of ordinary skill in the art after reading this document, the various implementations set forth herein can be implemented without confinement to the illustrated examples. For example, block diagrams and their accompanying description should not be construed as mandating a particular architecture or configuration. Similarly, in exemplary process flow charts, some blocks are optionally combined, the order of some blocks is optionally changed, and some blocks are optionally omitted. In some implementations, additional steps may be performed in combination with the exemplary processes. Accordingly, the methods and systems as described and illustrated in greater detail below are exemplary by nature and, as such, should not be viewed as limiting.

As used herein, the terms "full spectrum flow cytometry" and "full spectrum flow cytometer" refer to a technique and instrument, respectively, for performing flow cytometry where the instrument is configured to capture the full emission spectrum of fluorescent molecules using arrays of highly sensitive light detectors, thereby enabling the capture of highly multiplexed fluorescence intensity data sets.

As used herein, the term "immunophenotyping panel" refers to a panel of antibodies (e.g., fluorescently-labeled antibodies) that are used to identify cells based on the types of antigens or markers (e.g., cell surface receptor proteins) present on the surface of the cells.

The section headings used herein are for organizational purposes only and are not to be construed as limiting the subject matter described. The description is presented to enable one of ordinary skill in the art to make and use the invention, and is provided in the context of a patent application and its requirements.

Methods for Immune System Phenotyping and Automated Cell Classification

As described above, certain programmatic approaches for finding high dimensional clusters of labeled immune cells and purpose-built algorithms for defining high-dimensional clusters in immunespace exist. However, these approaches and algorithms have many shortcomings as described, for example, in the several FlowCAP challenges publications (see, e.g., Aghaeepour, et al. (2013), "Critical Assessment of Automated Flow Cytometry Data Analysis Techniques", *Nature Methods* 10(3):228-239).

As further described above, certain automated cell gating approaches for flow cytometry applications are known. However, these prior approaches rely on identification of patterns in the aggregate flow cytometry event distributions and on clustering-first approaches, and do not leverage an ensemble of machine-learning models that classify individual cell identities.

Overall, current immunophenotyping platforms (including high-throughput approaches) have several limitation, including the following two issues: (1) phenotyping platforms are constructed for a specific purpose and are by design different enough so as to confound data comparison between different experiments and across different immunophenotyping panels, and (2) the manual labor required to establish counts and/or frequencies of immune cells in the distinct immune cell sub-populations identified by an immunophenotyping panel is prohibitive to scaling the analysis to more than a few thousand samples. For existing platforms and approaches, the immunophenotyping panels used in different experiments are not comparable, and existing automated gating methods must be configured on a per-experiment basis that is only applicable for that experiment. The results of the immune profiling experiment are thus not generalizable Accordingly, there is a need for improved immunophenotyping platforms and methods.

Disclosed herein are immunophenotyping platforms (also referred to as immune profiling platforms) and methods that may address one or more of the above-identified shortcomings and needs. The immunophenotyping methods disclosed herein comprise performing high throughput, full spectrum flow cytometry in the context of an immunophenotyping processing pipeline comprising several stages: sample processing, data generation, raw data analysis, and results analysis. The disclosed immunophenotyping platforms and methods, combined with the novel application of machine learning algorithms as disclosed herein, may provide an expandable, high-throughput, and automated method that addresses the above-identified shortcomings and needs.

The immunophenotyping platforms disclosed herein provide the ability to process a blood sample from an individual (or any other single-cell suspension of immune cells extracted from a tissue sample) and generate an immune signature for the individual using full spectrum flow cytometry. Although described primarily in the context of immune profiling, the disclosed immunophenotyping platforms and methods can also be used more generally to generate cell type profiles based on FSFC analysis of any blood sample (or other single cell suspension) for which a suitable panel of fluorescently-labeled antibodies directed to an appropriate set of distinguishing cell surface antigens can be assembled.

In some instances, whole blood samples may be processed using FSFC to generate a fluorescence profile for each cell (e.g., each immune cell) within the sample. In some instances, blood samples may be processed to extract immune cells, and the immune cells may then be processed using FSFC to generation a fluorescent profile for each immune cell extracted from the sample. These profiles may then be used to generate an immune profile for the individual. This can be a highly standardized process that produces directly comparable results for analyses performed in different labs or at different times. In some instances, these results are used to train the machine learning models used to predict what category of immune cell type (i.e., to which distinct immune cell sub-population) each cell detected belongs. Together, the disclosed immunophenotyping platform and machine learning training and prediction frameworks enable the generation of clinically-relevant reference ranges for immune cell subtypes and support diagnostic decisions by leveraging the standardization of sample processing and machine learning-based automation of flow cytometry data processing in a scalable and less biased approach.

The immunophenotyping platforms and methods disclosed herein differ from existing platforms and methods in that other platforms do not provide comprehensive immune system level cell phenotyping at high sample processing throughput. Existing platforms are focused on a specific solution to a specific scientific question. The methods disclosed herein allow an integrated, automated, and standardized approach to producing high resolution immune profiles from blood samples at unprecedented speed and scale. The standardization and high sample throughput nature of the platform (e.g., up to 100, 150, 200, or 250 samples processed per FSFC instrument per 8 hour work day) enables establishing biological reference ranges for cell types or subtypes (e.g., immune cell subtypes) for human populations which will lead to better patient stratification and improved clinical diagnostic applications.

The platform and methods disclosed herein leverage full spectrum flow cytometry (FSFC) coupled with machine learning algorithms to analyze cells labeled using a standardized set of immune system status antibody panels. This represents the first comprehensive and standardized immunophenotyping platform with automatic cell classification. Firstly, all biological samples processed by the FSFC instrument are treated using a highly standardized and tightly controlled protocol that is subject to quality control (QC) standards. Secondly, the training and application of bespoke machine learning models to analyze the resulting flow cytometry data enables generation of immune profiles for blood samples on a timeline measured in hours.

Previous attempts at classifying immune cell identity are based on a clustering approach that is similar to that used in manual gating. The ML-based data analysis pipeline disclosed herein differs from previous approaches in that it examines each cell's fluorescent signature and classifies it based on an ensemble of gradient boosting machine learning models. Hence, identification of immune cell clusters and their hierarchical positioning are a byproduct of individual cell identification and classification by application of the trained ensemble model that comprises several thousand individual machine learning models, and are not based on identification of clusters first, and then measuring the correspondence of individual cells to the identified clusters.

FIG. 1 provides a non-limiting example of a process flow diagram for an immune profiling method 100 as disclosed herein. As shown, blood samples (or in some instances, buffy coat samples, peripheral blood mononuclear cell (PBMC) samples, or cell suspensions, etc.) are received at the laboratory facility, the sample is prepared 102 (e.g., comprising performing one or more of a dilution step, a centrifugation step, a staining step (using one or more fluorescently-labeled antibody panels) and/or a wash step) and analyzed on the full spectrum flow cytometer (FSFC) 104 resulting in the creation of a flow cytometry standard FCS file (comprising flow cytometry data) for the sample that is stored in a database 106. The FCS file may comprise, for example, fluorescence intensity data for one or more fluorescence detection channels (e.g., 2, 3, 4, 5, 6, 7, 8, 9, 10, 11, 12, 13, 14, 15, 20, 25, 30, 35, 40, 50, or more than 50 fluorescence detection channels), as well as data derived therefrom (e.g., forward scatter height data, forward scatter area data, side scatter height data, side scatter area data, autofluorescence data, or any combination thereof). In some instances, the number of fluorescence detection channels available may be determined by, for example, a combination of the detection hardware available as part of the flow cytometry instrument (e.g., comprising 5, 10, 20, 25, 50, 75, 100, 125, 150, 175, 200, or more than 200 detectors) and the number of spectrally-distinct fluorophores (e.g., 5, 10, 20, 25, 30, 35, 40, 45, 50, 60, or more than 60 spectrally-distinct fluorophores).

During a training phase, the data for several FCS files may be manually gated (e.g., by an immunologist or other expert) to generate labeled training data sets for one or more samples (e.g., control samples), and machine learning models (e.g., the individual models in an ensemble machine learning model) are trained 108 using the one or more labeled training data sets. These training sets are full instances of the gating hierarchy implemented on the FSFC output for a sample (e.g., a blood sample). The output of the gating process is a set of industry standard FlowJo workspace files describing the immunophenotyping classification hierarchy associated with their respective samples. The gating data encoded in these files is then extracted and fed through a cascading ensemble machine learning hierarchy which follows the same gating procedure. Within the hierarchy, each node represents an execution pipeline which trains and persists a singular ML model that predicts events specific to the corresponding biological cell type for that position in the hierarchy. These models are trained using the designated fluorescent channel data and gate location parameters provided by domain experts.

In some instances, the disclosed immunophenotyping and automated data analysis platform may use a single machine learning model to classify all cells within a cell populations. This can work well for some cell populations, but for populations where the true number of positive classes (cell subtypes) is small (e.g., less than about 100), the class imbalance can overwhelm the ability of a single ML model to reliably classify cell detection events. Weighting the smaller class detection events produces extremes in the case of misclassification (especially apparent as the class imbalance grows) that cause the model performance to degrade. In some instances, gradient boosted machine learning approaches (e.g., gradient boosted ensemble models) may provide superior performance.

The trained machine learning models 110 are then used to produce predictions of cell type or subtype (e.g., immune cell sub-population) for individual cell detection events and to determine cell counts (or frequencies) for each of a plurality of distinct cell types or subtypes which are then combined into an immune profile 112.

As noted above, processing of samples (e.g., blood samples) 102 may comprise one or more steps, including a staining step that comprises contacting cells within at least a first aliquot of the sample with at least a first panel (i.e., an immunophenotyping panel or FSFC panel) of fluorescently-labeled antibodies directed to a set of specific cell surface antigens (e.g., cell surface proteins) that collectively enable discrimination between the cell types or cell subtypes of interest. Sample processing may also include immunophenotyping panel design. A sample processing platform may comprise contacting each of one or more sample aliquots (e.g., 1, 2, 3, 4, 5, 6, 7, 8, 9, 10, or more than 10 sample aliquots) with one or more FSFC panels (e.g., 1, 2, 3, 4, 5, 6, 7, 8, 9, 10, or more than 10 FSFC panels).

For example, in some instances, each of two sample aliquots may be stained with a different FSFC panel, one focusing on the antigen-presenting cell (APC) arm of the immune system (A panel), which comprises antibodies directed to 36 different cell surface proteins, and the other focusing on the adaptive arm of the immune system (T panel), which comprises antibodies directed to 41 different cell surface proteins. In some instances, the panels may also include cell viability staining to distinguish between live cells and dead cells. In some instances, the panels may also comprise an autofluorescence measurement as a "marker". Specific examples of the cell surface proteins and additional markers that may be included in these panels are listed in Table 1.

TABLE 1

Non-limiting examples of cell surface receptor proteins and other markers for distinguishing between immune cell sub-populations.

| APC panel markers (A panel) | T panel markers (T panel) |
| --- | --- |
| IGM, LIVE_DEAD_BLUE, CD5, CD62L, CD294, CD69, CD38, PD1, CD11C, CD3, CD8, HLADR, CD24, CD337, CD123, CD141, Autofluorescence 1, CD1C, CD4, TACI, CD319, CD335, PDL1, CD10, CD45, CD16, IGD, CD40, CD19_TCRGD, CD43, CD14, CD138, CD15, CD56, CD86, CD303, CD27 | TIGIT, CD5, CD28, CXCR5, CD39, TIM3, CD38, PD1, TCRVA7_2_TCRVD1, CD95, CD3, CD8, HLADR, CD31, CCR4, CCR6, CCR7, Autofluorescence 1, CD57, ICOS, CD4, KLRG1, TCRVA24_JA18, CD122, CD103, CXCR3, TCRVD2, CD45, CCR10, CD16, CD25, CD161, CD19_TCRGD, LAG3, CD14, CD45RO, CD56, CD127, CD45RA, CD27 |

These panels are custom to the immunophenotyping platform disclosed herein, and are designed to be a maximally comprehensive view of the state of the sample donor's immune system. The panels include markers for determining immune cell type, immune system activation, lineage (e.g., the main marker(s) that are commonly used to define a certain cell population prior to further subsetting the cell type; examples include, but are not limited to, CD3 to define total T cells, and CD56 and CD16 to define natural killer cells), and exhaustion (cells that express markers associated with "cell exhaustion" (e.g., PD-1, TIGIT) can no longer proliferate and lose their functionalities as a result of chronic stimulation/prolonged activation of immune response). The immunophenotyping platform also defines a common hierarchy (a.k.a, a gating tree) that is used to process the fluorescence profile data for each detected cell and determine which and how many cells belong to each measured population (e.g., immune cell sub-population) in the hierarchy. This comprises 200+ gates for the APC panel and 2000+ gates for the T cell panel for the current configuration of the platform.

As part of panel design, it can be advantageous to define the maximum number of different fluorescent dyes that can be used within a single panel (which is related to the number of different fluorescence detection channels available in the FSFC instrument) to maximally cover the available spectrum whilst also providing clearly distinguishable signals to distinguish cell surface markers from each other. Multiple iterations may be leveraged to determine panel design parameters, and biological constraints may be leveraged to multiplex dye usage (e.g., Gamma Delta (GD) T cell receptors (TCR GD) may not be expressed on B cells, therefore the same fluorophore conjugated to anti-CD19 and also anti-TCR GD antibodies may be used, for identifying B cells and GD T cells respectively).

Furthermore, for panel design, it can be advantageous to minimize the sample (e.g., blood) volume required to process a sample. In some instances, the process described herein uses whole blood directly instead of isolating peripheral blood mononuclear cells. This may allow for the determination of granulocyte counts and frequencies.

Referring back to FIG. 1, data generation may refer to the largely automated data generation pipeline that comprises performing full spectrum flow cytometry 104 on the prepared blood sample to produce raw immunofluorescence intensities for each detected cell (e.g., immune cell), and register the output into database 106. In some instances, e.g., where two immunophenotyping panels are used to stain aliquots of the blood sample (such as the A panel and T panel described above), this process produces two data sets, e.g., a data set corresponding to each of the two immunophenotyping panels. In some instances, automated data transformation (e.g., a mathematical transformation of the fluorescence intensity data, or data derived therefrom, to minimize the impact of outlier data points) may be triggered by FCS file deposition onto the FSFC instrument hard drive. The transformed data may then be used as input for a machine learning model configured to classify individual cells according to cell type or sub-type.

Any of a variety of supervised machine learning models may be used to implement the methods and systems described herein. Examples include, but are not limited to, neural networks (e.g., deep neural networks), decision trees, and random forests.

In some instances, the disclosed methods and systems may be implemented using an ensemble machine learning model comprising a plurality of individual machine learning models. For example, in some instances, the disclosed methods and systems may be implemented using an ensemble machine learning model configured to process the fluorescence intensity data, or data derived therefrom, and classify individual cells of the plurality of fluorescently-labeled cells as belonging to one of a plurality of distinct immune cell sub-populations.

In some instances, the ensemble machine learning model may be organized in, for example, a cascading hierarchical tree structure comprising a plurality of nodes, where each node comprises an individual machine learning model. In some instances, each individual machine learning model comprises one input data set and up to eight output data sets (e.g., 1, 2, 3, 4, 5, 6, 7, or 8 output data sets) corresponding to branches of the cascading hierarchical tree structure. In some instances, each individual machine learning model may comprise a neural network model. In some instances, each individual machine learning model may comprise a gradient descent boosted tree model. In some instances, the plurality of nodes (i.e., the number of individual machine learning models in the ensemble) comprises at least 1000, 1200, 1400, 1600, 1800, 2000, 2200, or 2400 nodes. In some instances, the number of individual machine learning models in the ensemble machine learning model is equal to a number of distinct immune cell sub-populations in the plurality of distinct immune cell sub-populations.

In some instances, the design of the cascading hierarchical tree structure may be based at least in part on an expert analysis of manually-gated fluorescence intensity data, or data derived therefrom, for one or more samples, e.g., control samples as described elsewhere herein. In some instances, individual cells may be classified by the machine learning model (e.g., an ensemble machine learning model) independently of all other cells in the plurality of fluorescently-labeled cells contained within a sample. In some instances, individual cells may be classified recursively with all other cells of the plurality of fluorescently-labeled cells within a sample.

As noted above, the machine learning models (e.g., the individual models in an ensemble machine learning model) are trained during a training phase 108 using labeled training data sets generated using one or more FCS files for one or more samples (e.g., control samples) that are manually gated, e.g., by an immunologist or other expert. In some instances, the one or more samples may comprise whole blood samples. In some instances, the one or more control samples may comprise, e.g., cell suspensions comprising purified or partially purified cells of a single or only a few cell types or subtypes. Training and predictions may be periodically updated when advances in model architecture are made, more appropriate hyperparameters are identified, or new data is available.

In some instances, the individual machine learning models in the ensemble machine learning model may be trained individually using one or more labeled training data sets. For example, during training, an individual model's predictions may be used to validate the individual model but may not be propagated forward through the ensemble machine learning model, in order to minimize or eliminate error propagation during the training process.

In some instances, the individual machine learning models in the ensemble machine learning model may be trained collectively, e.g., using a recursive training method.

In some instances, the training of the ensemble machine learning model (or the individual models contained therein) may be controlled by one or more hyperparameter values that are the same for every node (individual model) in the cascading hierarchical tree structure. In some instances, the training of the ensemble machine learning model may be controlled by one or more hyperparameter values that are different for every node (individual model), or different for a subset of the nodes, in the cascading hierarchical tree structure. In some instances, the training of the ensemble machine learning model may be controlled by one or more hyperparameter values that are determined by performing a random grid search of the value ranges for the one or more hyperparameters.

Referring back to FIG. 1, data analysis may refer to the automated application of a trained a machine learning model (e.g., an ensemble machine learning model comprising 2200+ individual machine learning models) 110 to the raw data files generated by the FSFC instrument and stored in database 106. The cascading hierarchy of the ensemble machine learning model processes all or a portion of the fluorescent intensity readings (or data derived therefrom) from each cell and predicts the identity of the cell (i.e., the cell type or sub-type (also referred to herein as the cell sub-population) to which it belongs) as determined by the gating hierarchy defined by the immunophenotyping panel design.

Each ML model's input may use the same set of cell surface markers that an expert would use to analyze the data at that level of the hierarchy. For instance, to determine events that are identified as Neutrophils, an expert would look at a 2-dimensional plot with side scatter area on one axis and the fluorescent intensity of the CD16 marker on the second axis. The machine learning model at that node in the hierarchy may use the same two inputs. These inputs represent the encoded values of a proxy of the size and the amount of the marker (measured as the intensity). These input channels are optionally selected to mimic as closely as possible what the expert uses without including noise from the other channels which can overwhelm the signal provided. Biological expertise guides the selection of each channel for each immune population subset in the ML ensemble. Each ML model's input may also be the complete set of fluorescent channels available in the panel.

The ensemble ML models work together to produce accurate predictions of cell types for the entire gating hierarchy. During prediction, the ML models are arranged programmatically so that the top level model forwards its predictions to the next layer of models, e.g. the white blood cell (WBC) model uses two proximate size parameters (side scatter area vs. side scatter height) to determine if a cell detection event is likely due to the cell being a WBC. All of the events that are classified as WBC events may then be further predicted using one or two ML models and classified into side scatter high (SSChi) and side scatter low (SSClo) event types using the forward scatter (FSC) and side scatter (SSC) channels. Cell detection events that are predicted as SSChi are then further characterized to determine if they are positive for expression of the CD15 cell surface marker. Each step of this process is performed by a specific ML model trained for this explicit purpose. This process is followed for each node in the gating hierarchy.

The machine learning platform 110 produces cell type or subtype predictions at each leaf (i.e., final node having no child nodes) in the defined gating hierarchy independently using one or multiple machine learning models, which may have the same or different architectures, working together in an ensemble. The predictions from these models can either be recursively cascaded through the hierarchy from more general to more specific (e.g., from parent to child) or each cell may be classified independently of all other cells and all other gating hierarchy decisions.

The trained machine learning model(s) may be configured to classify individual cells as belonging to one of a plurality of distinct cell sub-populations, e.g., immune cell sub-populations. In some instances, the plurality of distinct cell sub-populations (e.g., distinct immune cell sub-populations) may comprise at least 1000, 1200, 1400, 1600, 1800, 2000, 2200, or 2400 distinct immune cell sub-populations.

Non-limiting examples of immune cell sub-populations (or sub-types) that may be identified using, e.g., the A panel and T panel sets of fluorescently-tagged antibodies described above are illustrated in Table 2.

TABLE 2

| Non-limiting examples of immune cell sub-populations identified using A panel and T panel antibodies. | |
|---|---|
| APC panel (A panel) populations | T panel populations |
| WBC | T-cell |
| Eosinophil | iNKT |
| Eosinophil/CD5+ | Total GD |
| Neutrophil | Vd1 |
| Neutrophil/Big | Vd2 |
| Neutrophil/CD5+ | Vdx |
| Neutrophil/small | MAIT |
| B-cell | TEMRA |
| B-cell/CD5− CD27− | CD4 NAÏVE |
| Monocyte/CD56+ | T_HELPER |
| Monocyte/CD56− | CD4 Effector Memory |
| NK-cell | Treg |
| DC | (and 2000+ additional |
| (and 180+ additional | sub-populations) |
| sub-populations) | |

Figure 2:
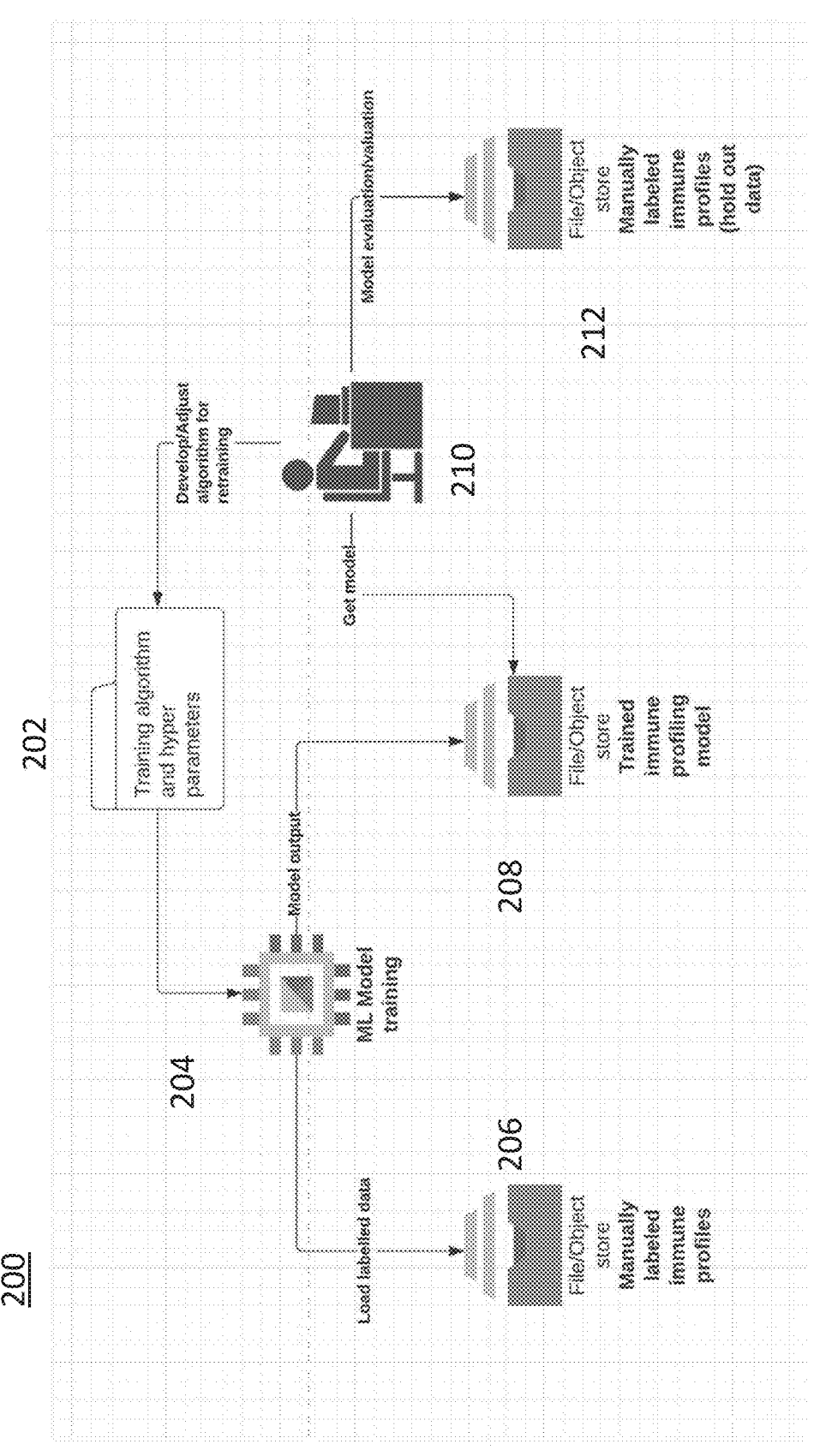
FIG. 2 provides a non-limiting example of a process flow diagram for a method of training an ensemble machine learning (ML) model, according to one embodiment as described herein.

FIG. 2 provides a non-limiting example of a flow diagram of a machine learning training process 200. Domain experts may produce and store manually labeled training data 206 from selected FCS files. Machine learning specialists may define machine learning architecture, training algorithms, and hyperparameters 202 to generate ML scripts. The ML scripts may be then executed to train the machine learning model(s) 204 on a selection of manually labeled data 206, and subsequently stored in database 208. The output models may be validated using a hold-out data set 212 that has also been manually labeled by an expert. The results of the validation may be manually reviewed by data science experts and/or biologists 210. Models failing validation may be tuned and retrained.

The training data used to train the machine learning models may be manually produced using a subset of expertly gated exemplar immunophenotyping outputs. These manually gated cells may be used to train the machine learning model to be able to identify similar cells based on the fluorescence profile characterized by the spectral flow cytometer for a given cell type or subtype.

In some instances, the use of training data generated by multiple experts may remove bias from the gating process, so replacing the automated gating process with manual gating may produce different (and potentially erroneous) results.

As noted above, machine learning model predictions may be validated against a hold-out set of manually gated files generated by domain experts using prediction metrics which are relative to the manually-gated hold-out set. Examples of prediction metrics include, but are not limited to, comparison of the means of cell population distributions from the predicted set to within 5%, 10%, 20%, 30% of those for the hold-out set; comparison of standard deviations of cell population distributions from the predicted set to within 5%, 10%, 20% of that for the hold-out set; and/or correlations between cell population ratios for the predicted set to cell population ratios for the hold-out set of greater than 85%, 90%, 95%, or 98%. A correlation of 100% means that the ML model predicted exactly the same cell population ratios as were determined by manual gating.

In some instances, the threshold for determining validity of the ML model predictions can be modulated by thresholding the standard deviation differences using a standard deviation difference threshold of, e.g., less than 5%, 10%, 15%, or 20%.

In some instances, the threshold for determining validity of the ML model predictions can be modulated by thresholding the correlation using a correlation threshold of greater than 80%, 85%, 90% 95%, or 98%.

The models that pass validation may be accepted as good predictors and stored in database 208. Remaining models may be cycled through one or more additional rounds of training by data science experts and/or biologists 210 with more training data, changes of algorithm, or hyperparameter tuning at each round until they pass validation.

In some instances, the machine learning model architectures may comprise, for example:
   a gradient descent boosted tree machine learning algorithm with up to a thousand trees;
   a deep neural network with typically between 2 and 4 hidden layers and up to 250 nodes per layer;
   a convolutional neural network with; and/or
   an autoencoder with, for example, up to 7 layers (e.g., 5 convolutions, 2 pooling).

The model hyperparameters are tunable per a specific application of model training.

Trained and validated models may be used to predict immune cell sub-population counts and frequencies on all appropriate samples. The results of the predictions on each cell sub-population within a given sample may be aggregated to produce a systems view of the immune state of the individual from which the sample was collected, which may form all or part of an immune profile.

Figure 3:
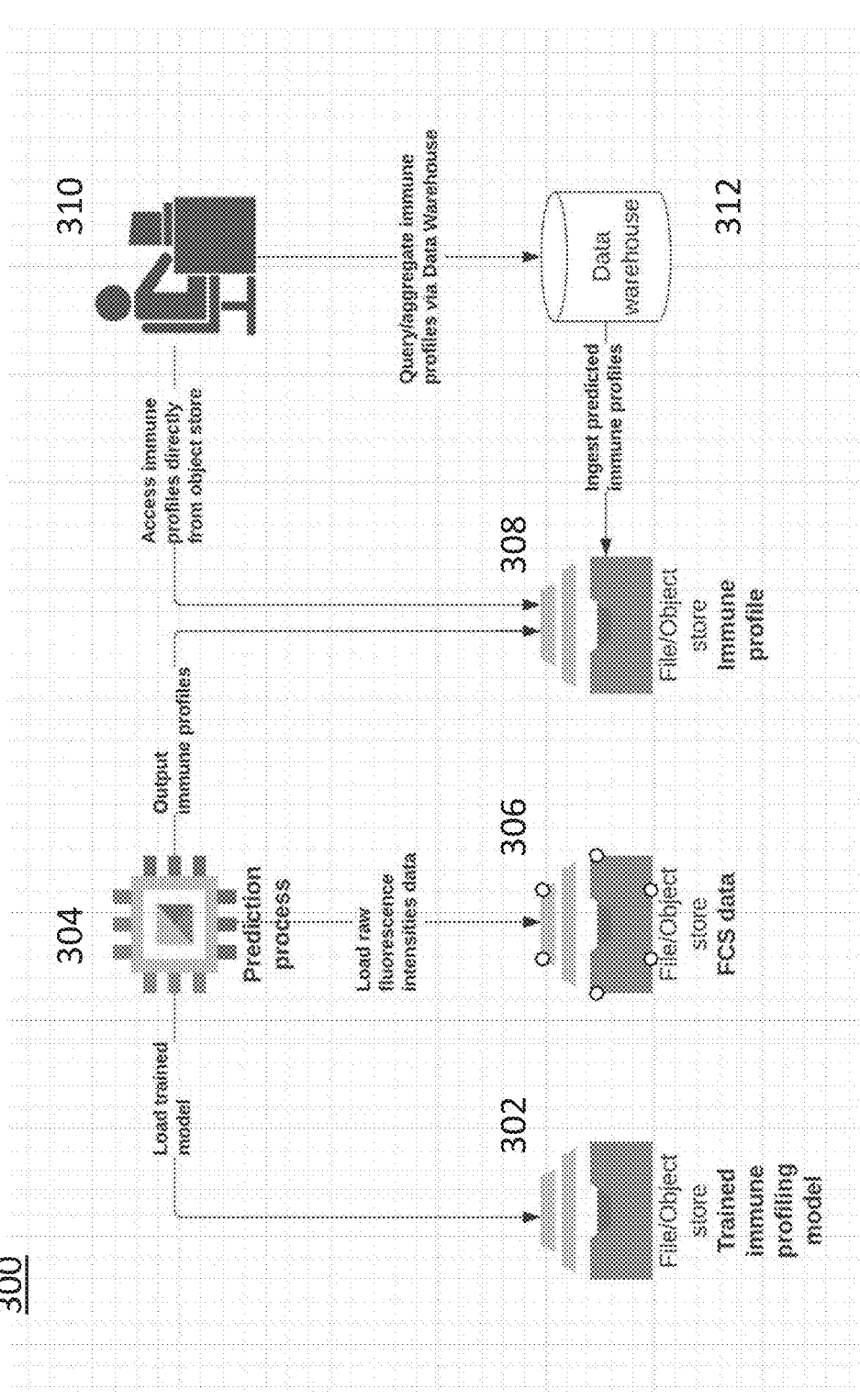
FIG. 3 provides an exemplary illustration of machine learning model-based prediction and immune profile generation, according to one embodiment of the methods and systems described herein.

FIG. 3 provides an exemplary illustration of a process 300 for machine learning model-based prediction and immune profile generation. Machine learning models that pass validation (stored in database 302) are applied to raw FCS files 306 to produce immune cell population count predictions 304. These predictions are collected into an immune profile (stored in database 308) and made available for further analysis 310, including, e.g., queries of aggregated immune profiles (e.g., aggregated according to an individual or patient's demographic or clinical data including, but not limited to, age sex, race, family history, disease diagnosis, etc.) stored in database 312.

Identification of the most appropriate machine learning algorithm and metadata parameters may be advantageous to help to produce high quality predictions on immune data. The system may be configured to use the most appropriate model architecture, and the model architecture may continue to be iterated. The training of the model(s) may also be updated periodically or continuously as new training data becomes available.

In some instances, an ensemble machine learning model comprising more than 2000 individual machine learning models may be used to perform automated analysis on a sample. Training and managing large numbers of machine learning models such as this may be accomplished by programmatic infrastructure. The platforms and methods disclosed herein may use a software platform to manage the application of trained machine learning models to raw flow cytometry data to produce cell count predictions.

Advantages of the platforms and methods disclosed herein may be provided by standardizing the immunophenotyping platform and enabling machine learning-based data processing automation. This enables the disclosed platforms and methods to go from highly complex FSFC data to translatable immune profiles for use in clinically-relevant timeframes (e.g., hours rather than days). In some instances, an immune profile for a sample may be generate in less than 24 hours, 12 hours, 10 hours, 8 hours, 6 hours, or 4 hours.

The output of the prediction process may include an immune profile. This profile may comprise the immune cell counts and/or sub-population frequencies of all measured cell sub-populations. These immune profiles represent a snapshot of the donor's immune system at the time of sample collection, and several longitudinal samples can be compiled to demonstrate an immune trajectory. Furthermore, several different donor immune signatures may be compiled to discover statistically significant population-level immune signatures. Display of these different use cases may be dependent on specific project requirements.

The methodology described herein may have advantages as compared to using different panels, different algorithms, and/or different automated gating approaches. Advantages may include generating more accurate and effective cell clustering, cell type or sub-type predictions, and immune profiles. The accuracy of the disclosed machine learning models may be evaluated for example, based on precision (e.g., the percentage of cells classified as being of a given cell type that are actually of that type), recall (e.g., the percentage of cells in a data set that are correctly classified as belonging to a given cell type), and F1 score (i.e., an accuracy metric that combines the precision and recall of a model to assess how many times the model made a correct prediction across the entire data set).

Applications

The disclosed methods and systems for generating immune profiles may be used for a variety of biomedical research and clinical diagnostic applications. Examples include, but are not limited to, diagnosis of immune-related diseases and disorders, diagnosis of autoimmune diseases and cancer, diagnosis of and/or identification of individual-specific response to infectious diseases, the prediction of response to treatment either prior to or during treatment, and the characterization of donors and products in cell therapy manufacturing.

Systems for Immune System Phenotyping and Automated Cell Classification

Also disclosed herein are systems designed to implement any of the disclosed methods for generating an immune profile for a sample from a subject. The systems may comprise, e.g., one or more processors, and a memory unit communicatively coupled to the one or more processors and configured to store instructions that, when executed by the one or more processors, cause the system to: receive fluorescence intensity data, or data derived therefrom, acquired using a full spectrum flow cytometer to process a fluorescently-labeled cell sample collected from a subject; provide at least a subset of the fluorescence intensity data, or data derived therefrom, for the plurality of fluorescently-labeled cells as input to an ensemble machine learning model configured to process the fluorescence intensity data, or data derived therefrom, and classify individual cells of the plurality of fluorescently-labeled cells as belonging to one of a plurality of distinct immune cell sub-populations; and output a total cell count or cell frequency for each of the plurality of distinct immune cell sub-populations in the sample as part of an immune profile for the subject. In some instances, the system may further comprise a full spectrum flow cytometer (FSFC) instrument.

Similarly, non-transitory computer-readable storage media are disclosed that may comprise instructions for operating a system configured to perform any of the disclosed methods for generating an immune profile for a sample from a subject. For example, non-transitory computer-readable storage media storing one or more programs are described, the one or more programs comprising instructions, which when executed by one or more processors of a system, cause the system to: receive fluorescence intensity data, or data derived therefrom, acquired using a full spectrum flow cytometer to process a fluorescently-labeled cell sample collected from a subject; provide at least a subset of the fluorescence intensity data, or data derived therefrom, for the plurality of fluorescently-labeled cells as input to an ensemble machine learning model configured to process the fluorescence intensity data, or data derived therefrom, and classify individual cells of the plurality of fluorescently-labeled cells as belonging to one of a plurality of distinct immune cell sub-populations; and output a total cell count or cell frequency for each of the plurality of distinct immune cell sub-populations in the sample as part of an immune profile for the subject.

Computer Processors & Computing Systems

Figure 4:
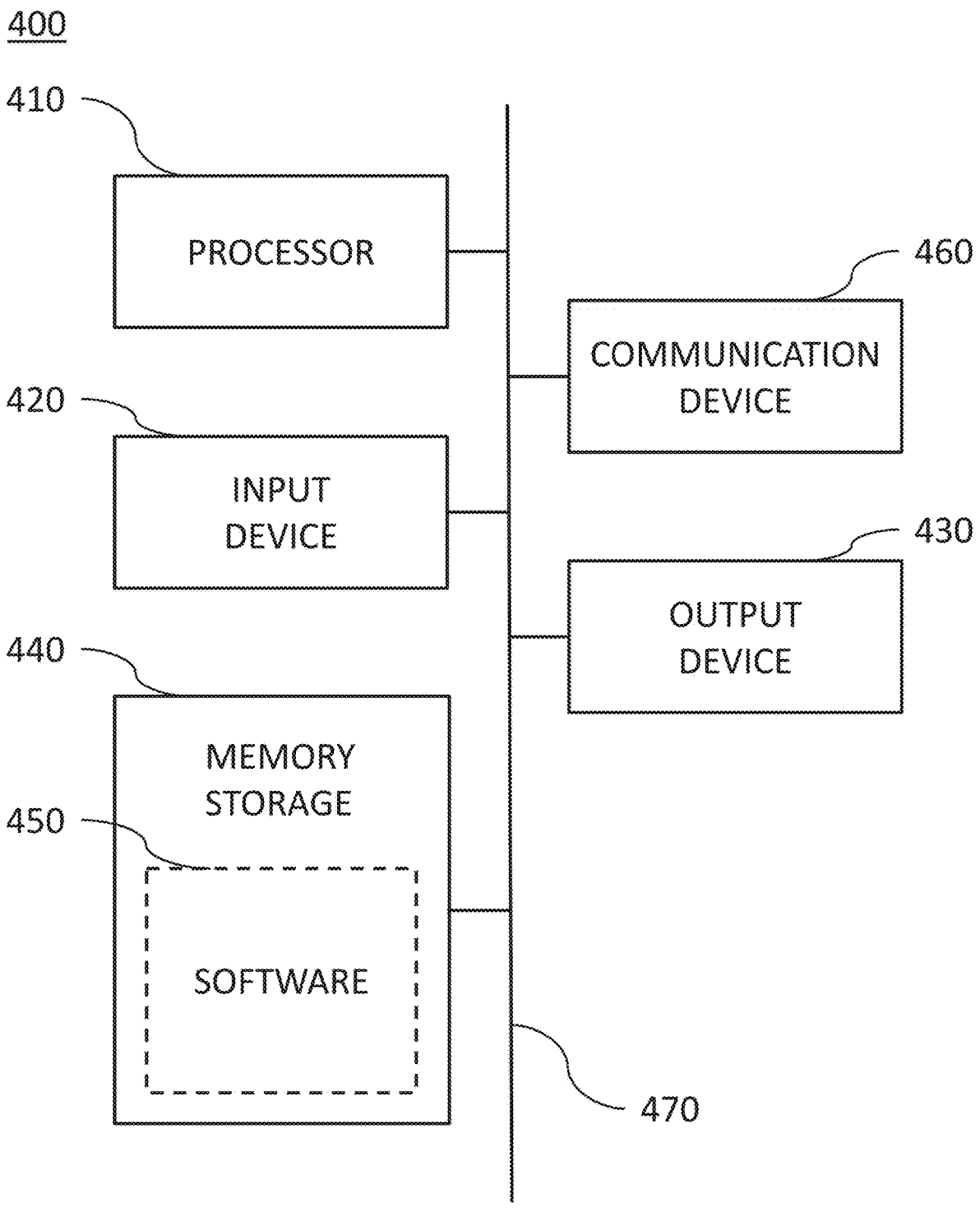
FIG. 4 illustrates an exemplary computing system, in accordance with some embodiments of the methods and systems described herein.

FIG. 4 illustrates an exemplary computing system, in accordance with some implementations. Computing system 400 can be a component of a system for generating an immune profile for a sample from a subject.

Computing system 400 can include a host computer connected to a network. Computing system 400 can be a client computer or a server. As shown in FIG. 4, computing system 400 can comprise any suitable type of microprocessor-based device, such as a personal computer; workstation; server; or handheld computing device, such as a phone or tablet. The computer can include, for example, one or more of processor 410, input device 420, output device 430, memory storage 440, and communication device 460.

Input device 420 can be any suitable device that provides input, such as a touch screen or monitor, keyboard, mouse, or voice-recognition device. Output device 430 can be any suitable device that provides output, such as a touch screen, monitor, printer, disk drive, or speaker.

Memory storage 440 can be any suitable device that provides storage, such as an electrical, magnetic, or optical memory, including a RAM, cache, hard drive, CD-ROM drive, tape drive, or removable storage disk. Communication device 460 can include any suitable device capable of transmitting and receiving signals over a network, such as a network interface chip or card. The components of the computer can be connected in any suitable manner, such as via a physical bus or wirelessly. Memory storage 440 can be a non-transitory computer-readable storage medium comprising one or more programs, which, when executed by one or more processors, such as processor 410, cause the one or more processors to execute any of the methods described herein.

Software 450, which can be stored in memory storage 440 and executed by processor 410, can include, for example, the programming that embodies the functionality of the present disclosure (e.g., as embodied in the methods, systems, computers, servers, and/or devices as described above). In some embodiments, software 450 can be implemented and executed on a combination of servers such as application servers and database servers.

Software 450 can also be stored and/or transported within any computer-readable storage medium for use by or in connection with an instruction execution system, apparatus, or device, such as those described above, that can fetch and execute instructions associated with the software from the instruction execution system, apparatus, or device. In the context of this disclosure, a computer-readable storage medium can be any medium, such as storage 440, that can contain or store programming for use by or in connection with an instruction execution system, apparatus, or device.

Software 450 can also be propagated within any transport medium for use by or in connection with an instruction execution system, apparatus, or device, such as those described above, that can fetch and execute instructions associated with the software from the instruction execution system, apparatus, or device. In the context of this disclosure, a transport medium can be any medium that can communicate, propagate, or transport programming for use by or in connection with an instruction execution system, apparatus, or device. The transport-readable medium can include, but is not limited to, an electronic, magnetic, optical, electromagnetic, or infrared wired or wireless propagation medium.

Computing system 400 may be connected to a network, which can be any suitable type of interconnected communication system. The network can implement any suitable communications protocol and can be secured by any suitable security protocol. The network can comprise network links of any suitable arrangement that can implement the transmission and reception of network signals, such as wireless network connections, T1 or T3 lines, cable networks, DSL, or telephone lines.

Computing system 400 can implement any operating system suitable for operating on the network. Software 450 can be written in any suitable programming language, such as C, C++, Java, or Python. In various embodiments, application software embodying the functionality of the present disclosure can be deployed in different configurations, such as in a client/server arrangement or through a Web browser as a Web-based application or Web service, for example.

EXAMPLES

The following examples are included for illustrative purposes only and are not intended to limit the scope of the present disclosure.

Example 1—Manual Gating of Full Spectrum Flow Cytometry Data

Figure 5:
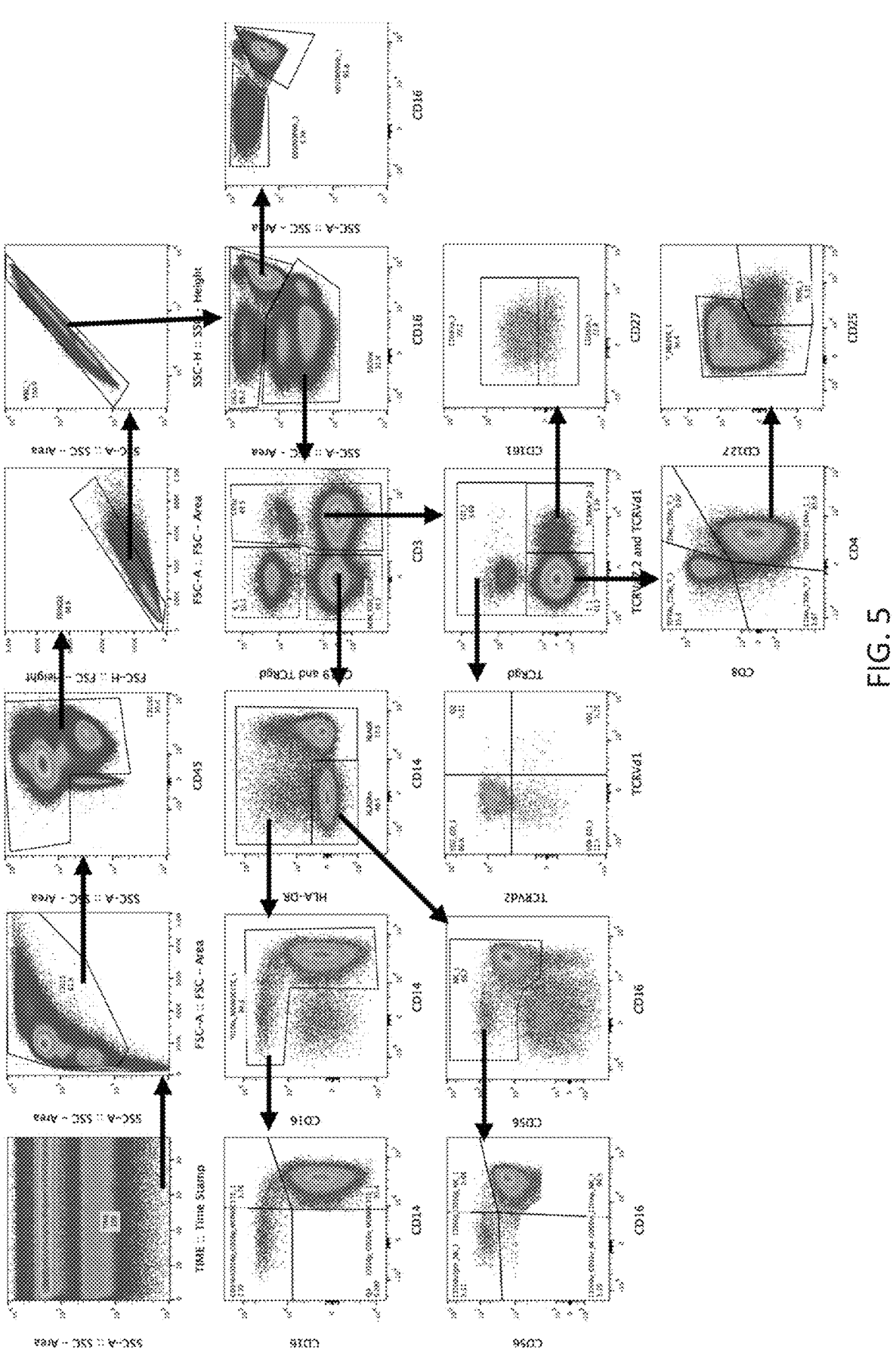
FIG. 5 provides a non-limiting schematic illustration of a manual gating process for processing full spectrum flow cytometry data.

One of the underlying principles of flow cytometry data analysis is "gating," which is the sequential identification and refinement of a cellular population of interest based on labeling a panel of cell type-specific molecules (also known as markers) using, e.g., fluorescently-labeled antibodies, that are detected by fluorescence (Verschoor, et al. (2015), "An Introduction to Automated Flow Cytometry Gating Tools and Their Implementation", *Frontiers in Immunology* Vol. 6, Article 380). FIG. 5 provides a non-limiting schematic illustration of a manual gating process for processing full spectrum flow cytometry data. Fluorescence intensity data, or data derived therefrom (e.g., forward scatter data, side scatter data, live cell/dead cell staining, autofluorescence, etc.), is generated by the FSFC instrument and reviewed by an expert practitioner. Cell types or sub-types are identified by selecting sections or subsections of the plotted fluorescence data (e.g., fluorescence intensity data plotted as heatmaps in the individual panels of FIG. 5) and refining it further using additional criteria, where each additional criterion applied to the analysis constitutes a "gate". The number of cell detection events circumscribed within each gate is equal to the number of cells identified for that cell population or sub-population. Exemplary gating criteria, as illustrated in FIG. 5, include SSC-A (side scatter-area), FSC-A (forward scatter-area), SSC-H (side scatter-height), FSC-H (forward scatter-height), CD45 (fluorescence signal arising from a fluorescently-labeled anti-CD45 monoclonal antibody), etc. The numbers associated with specified cell types in some of the panels indicate the percentage of cells from the previous gate that satisfied the current gating criteria.

Example 2—Training of a Neural Network Model for Immune Cell Type Classification This example provides an illustration of using pre-defined gates from an expert to train a machine learning model (e.g., a neural network) that accurately predicts an immune cell type. The initial assumptions underlying the development of the model included: (i) that FCS files include data for hundreds of thousands of cell detection events, (ii) each cell detection event represents a training opportunity, and (iii) a cell's type, sub-types, and status can be distinctly identified by its inclusion in a set of labelled gates.

Figure 6:
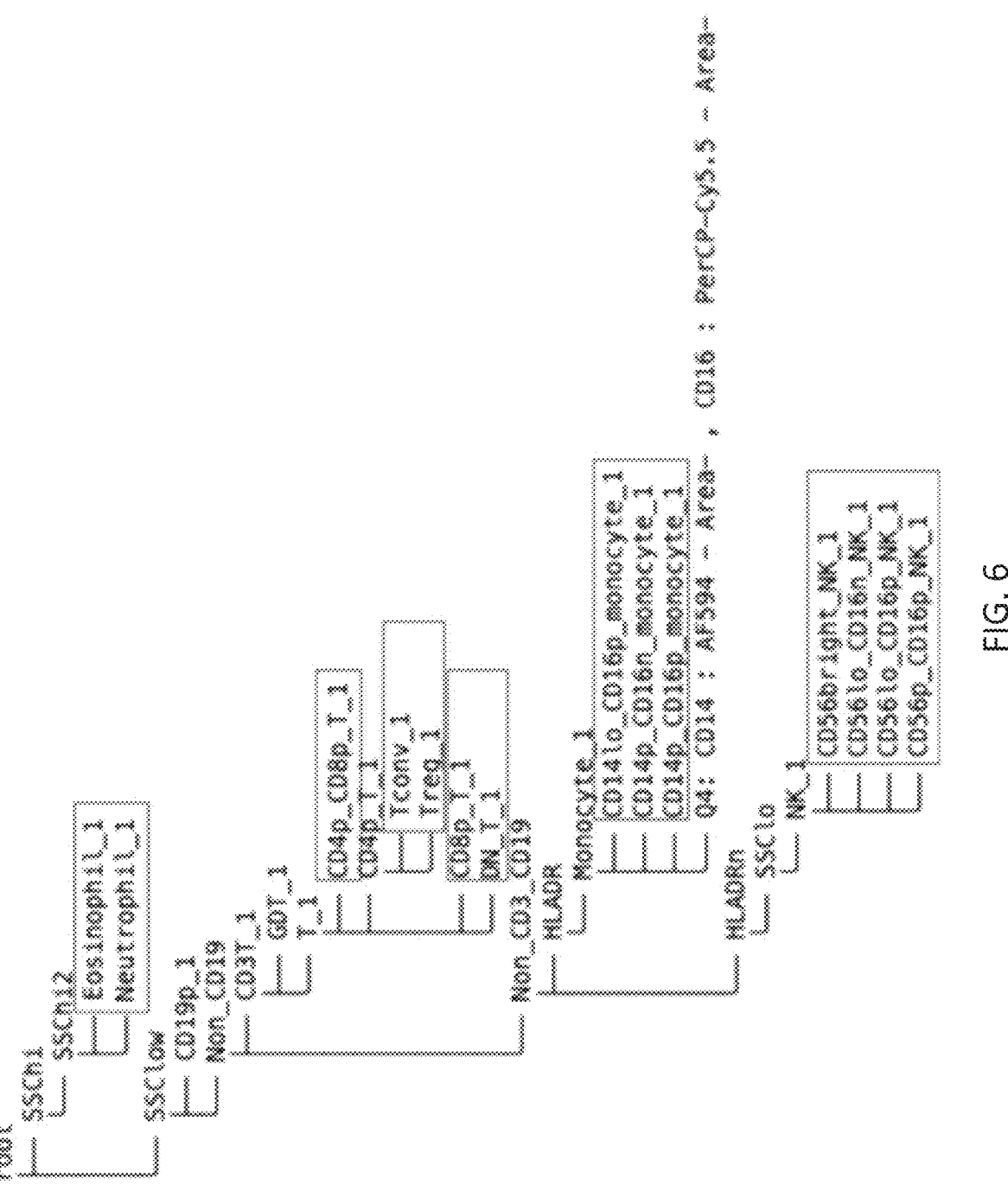
FIG. 6 provides a non-limiting example of a simplified gating hierarchy used to build a neural network for immune cell classification.

FIG. 6 provides a non-limiting example of a simplified gating hierarchy used to build a neural network for immune cell classification. Each node of the gating hierarchy represents a different immune cell type, sub-type or cell status. Starting from the root, side scatter high (SSChi) and side scatter low (SSClow) signals may be used, for example, to discriminate between white blood cells (eosinophils and neutrophils) and other immune cells. Fluorescent signals associated with labeling of appropriate cell surface markers may then be used to discriminate between eosinophils and neutrophils. As indicated in the gating hierarchy illustrated in FIG. 6, detection of fluorescent signals associated with labeling of other cell surface markers (e.g., CD19, CD3T, GDT, CD4, CD8, etc.) may be used to classify immune cells into a number of distinct immune cell sub-types.

Table 3 provides a non-limiting example of a panel of fluorescently-labeled monoclonal antibodies that may be used to detect cell surface markers (adapted from Mahnke, et al. (2012), "OMIP-013: Differentiation of Human T-Cells", *Cytometry Part A* 81A: 935-936).

TABLE 3

| Non-limiting examples of fluorescently-labeled monoclonal antibodies. | | | |
|---|---|---|---|
| Cell Surface Marker | Monoclonal Antibody Clone | Fluorochrome | Purpose |
| CD3 | SK7 | APC-H7 | Lineage |
| CD4 | M-T477 | QD605 | |
| CD8 | RPA-T8 | QD585 | |
| CCR7 | 150503 | Ax680 | Memory/ |
| CD27 | O323 | FITC | Differentiation |
| CD28 | CD28.2 | PE-Cy5 | |
| CD31 | WM59 | PE-Cy7 | |
| CD45RA | HI100 | APC | |
| CD57 | NK-1 | QD705 | |
| CD95 | DX2 | PE | |
| CD127 | A019D5 | BV421 | |
| CD244 | C1.7 | PE-Cy5.5 | |
| Dead cells | — | AqBlu | Dump |

APC, allophycocyanin; H7, highlight 750; QD, quantum dot; Ax, Alexa; FITC, fluorescein isothiocyanate; PE, R-phycoerythrin; Cy, cyanine; BV, brilliant violet; AqBlu, live/dead fixable aqua dead cell stain.

Figure 7:
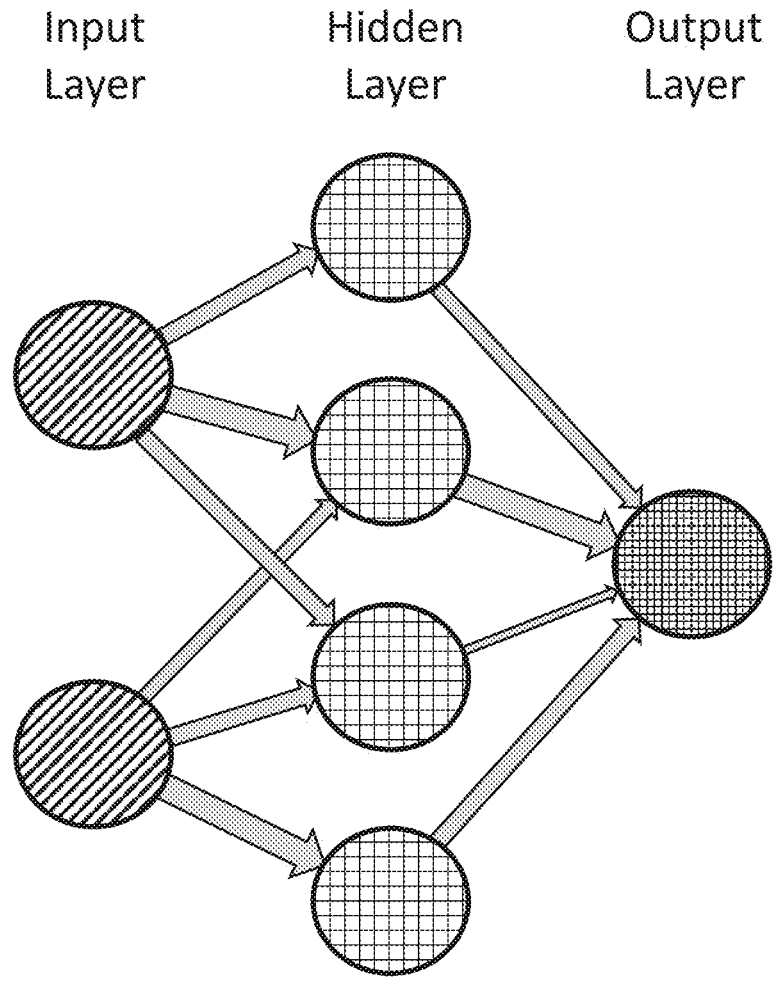
FIG. 7 provides a simplified schematic illustration of a neural network.

FIG. 7 provides a simplified schematic illustration of a neural network comprising an input layer comprising two or more nodes (or "perceptrons"), at least one hidden layer (comprising four or more nodes), and an output layer (comprising a single node in this non-limiting example). In general, the neural network may comprise any total number of layers, and any number of hidden layers, where the hidden layers function as trainable feature extractors that allow mapping of a set of input data to a preferred output value or set of output values. Each layer of the neural network comprises a number of nodes (or perceptrons). A node receives input that comes either directly from the input data (e.g., flow cytometry data, or data derived therefrom) or the output of nodes in previous layers, and performs a specific operation, e.g., a summation operation. In some cases, a connection from an input to a node is associated with a weight (or weighting factor). In some cases, the node may, for example, sum up the products of all pairs of inputs from a previous layer and their associated weights. In some cases, the weighted sum is offset with a bias, b. In some cases, the output of a node may be gated using a threshold or activation function, f, which may be a linear or non-linear function. The activation function may be, for example, a rectified linear unit (ReLU) activation function or other function such as a saturating hyperbolic tangent, identity, binary step, logistic, arcTan, softsign, parameteric rectified linear unit, exponential linear unit, softPlus, bent identity, softExponential, Sinusoid, Sine, Gaussian, or sigmoid function, or any combination thereof.

The weighting factors, bias values, and threshold values, or other computational parameters of the neural network, can be "taught" or "learned" in a training phase using one or more sets of training data. For example, the parameters may be trained using the input data from a training data set and a gradient descent or backward propagation method so that the output value(s) (e.g., immune cell classifications) that the neural network predicts are consistent with the examples included in the training data set. The adjustable parameters of the model may be obtained using, e.g., a back propagation neural network training process that may or may not be performed using the same hardware as that used for performing immune cell classification.

A neural network such as that illustrated schematically in FIG. 7 was trained using labeled training data split into training (typically 80% of the total) and test (typically 20% of the total) data sets. For each cell detection event in the training data set, data was matched to the appropriate input nodes, the neural network model performing an initial classification, the output was compared to the actual (known) output for the detection event, internal model weights were adjusted, and the cycle was repeated. The trained model was then tested by processing the reserved test data and comparing the model predictions for cell type to the actual (known) cell types. The performance of the model was evaluated using metrics such as precision and recall.

FIG. 8 provides a non-limiting example of test data generated by a trained neural network classifier. Support, indicated in the right-most column, is the number of cells classified by manual gating as belonging to the indicated cell type. The performance of the model was evaluated by calculating the precision, recall, and F1-score as described elsewhere herein for 16 immune cell types. Micro average: metrics calculated globally by counting the total number of true positives, false negatives and false positives. Macro average: metrics calculated for each label (cell type) to determine their unweighted mean (this does not take label imbalance into account). Weighted average: metrics calculated for each label to determine their average weighted by support (the number of true instances for each label). This weighted average alters the 'macro' calculation to account for label imbalance, and can result in an F-score that is not between precision and recall. Sample average: metrics calculated for each instance to determine their average (this calculation is only meaningful for multilabel classification where this differs from accuracy_score). As can be seen, the weighted average for precision and recall were 0.94 and 0.92, respectively, in this study.

FIG. 9 provides a non-limiting example of test data generated by a trained neural network classifier after training the model on a much larger training data set. As can be seen, the weighted average for precision and recall were 0.98 and 0.98, respectively, in this study.

FIG. 10 provides a non-limiting example of validation data (i.e., model prediction data for input data not previously provided to the model) for a trained neural network classifier. The weighted average for precision and recall were 0.99 and 0.98, respectively, in this validation run.

FIG. 11 provides another non-limiting example of validation data generated by a trained neural network classifier. The weighted average for precision and recall were 0.98 and 0.91, respectively, in this validation run.

Example 3—Application of an Ensemble Machine Learning Model to Automated Cell Counting An FCS file consists of metadata about the fluorophores and associated markers used when performing the flow cytometry experiment. It also includes data corresponding to each fluorescent channel for every event detected by the flow cytometer. The conventional approach to extract counts and frequencies of immune cell populations from a sample (such as determining the percentage of Neutrophils identified out of all white blood cells detected) from an FCS file involves using specialized software (e.g., FlowJo, BD Biosciences, Ashland OR). This manual method entails opening the file within the software, visually examining the events across multiple bivariate plots, and identifying cell clusters that conform with well-established biological phenotypes. It also requires leveraging the association between fluorescent dyes and immune cell surface proteins as defined by the immunophenotyping panel design. Subsequently, enclosing polygons are manually created to delineate clusters of immune cells in a two-dimensional space, aligning with background immunology expertise in looking at cell surface marker distribution. When all immune cell subsets of interest have been identified using this method (2000+ in the case of the IMU (IMU Biosciences, London, UK) phenotyping panel), a signature of cell population ratios can be extracted.

To increase the speed and accuracy of this process of cell counting and classification, automated cell classification can be applied. Given a standard gating hierarchy, a set of FCS files, and a set of reference configurations of each gate stored in manually gated workspace files, an ensemble machine learning model can be trained to determine a cell population signature. The ensemble machine learning model comprises a set of individual ML models, where each ML model of the set is trained to predict if an event falls inside or outside of a configured gate. Once the set of models is trained, a signature can be constructed without manual intervention as follows.

For each event in the FCS file, the machine learning ensemble is invoked. Every node in the ensemble may consist, for example, of one machine learning model configured to receive input from each fluorescent channel, where the machine learning model has an internal state that was learned during the training stage, and outputs a set of events that are predicted to be enclosed by the defined gate represented within the ML model. These ML-filtered events are then cascaded into one or several predicted output categories corresponding to the number of children gates at the next level of the gating hierarchy. The set of machine learning models in the ensemble are organized in a directed acyclic graph structure, with the root node being the first filter in the gating hierarchy. To begin the process of predicting an immune signature, the complete set of events in the FCS file is passed as input into the root machine learning model. Events that conform to the gating definition contained in the ML model are retained and provided as input to the next model (or models) in the hierarchy. Every node in the hierarchy represents an immune cell type or status and when the process is complete, all the counts and frequencies of all nodes can be extracted to comprise the complete immune signature for that data file.

Figure 12:
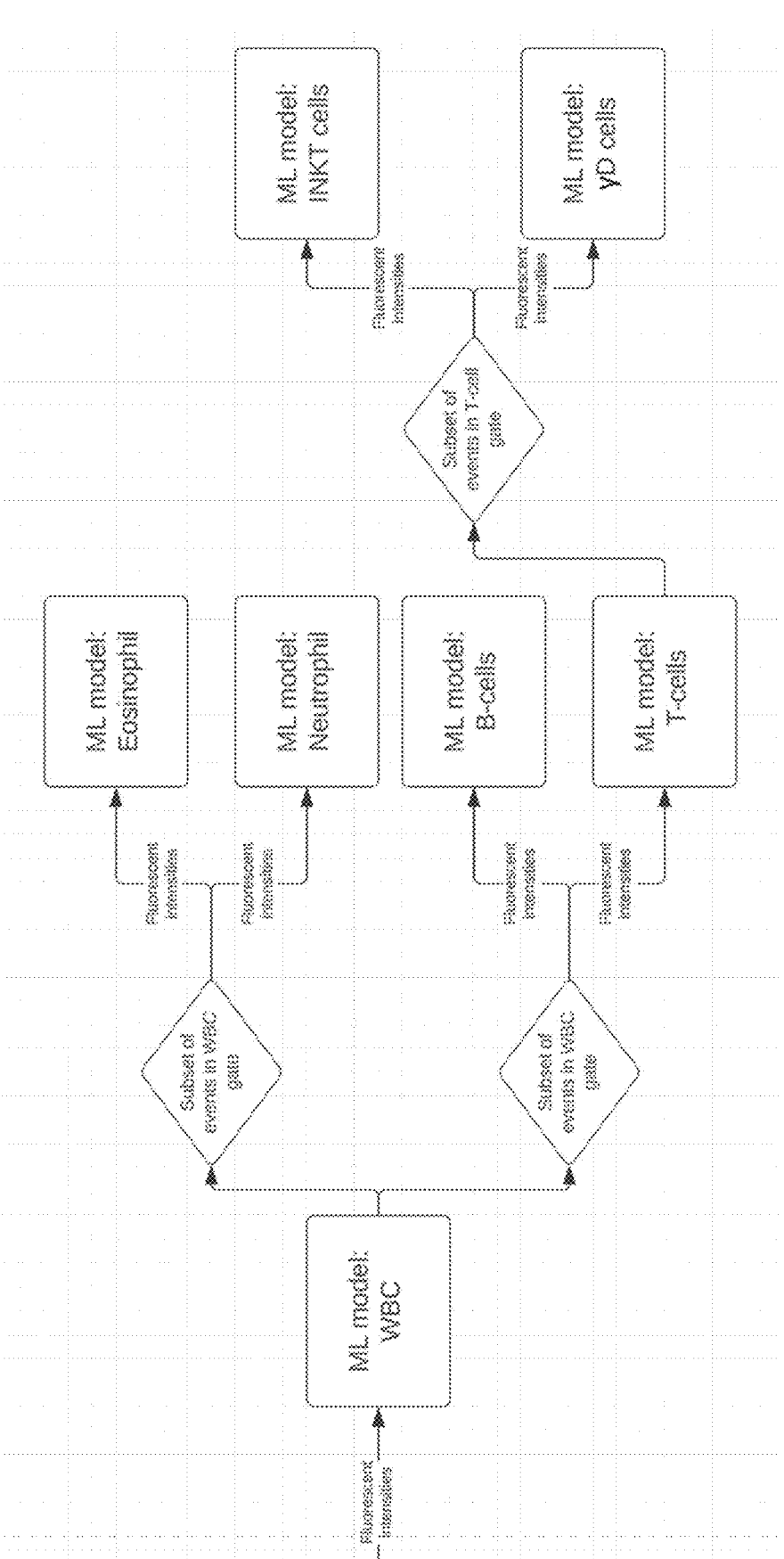
FIG. 12 provides a non-limiting example of the data flow through cascading predictions from node to node, i.e., from parent ML model output to child/children ML model inputs in an ensemble machine learning model.

FIG. 12 provides a non-limiting example of the data flow through cascading predictions from node to node, i.e., from parent ML model output to child/children ML model inputs. In this example, fluorescence intensities are input to the root node (white blood cell (WBC)) model, and individual detection events are classified into two output categories (WBC subtypes). The fluorescence intensity data for the latter are then input into the next set of models in the gating hierarchy, e.g., either an Eosinophil ML model and Neutrophil ML model, or a B-cell ML model and T-cell ML model. As indicated in the illustration, the fluorescence intensity data for a subset of T-cell gated events may then be input into, e.g., an INKT cell ML model or a TD cell ML-model.

Example 4—Application of Immune Signatures to Highlight Biologically Meaningful Insight To demonstrate the effectiveness of the disclosed immunophenotype profiling method to identify and correct for changes in general health lifestyle and health factors of a donor sample, an analysis was performed to determine to what extent vitamin D fluctuations impacted parameters of the immune system. A dataset of 609 donors was assembled (58% female, age 38.7±12.5 years), fresh blood collected and analyzed using the FCSC approach defined herein. In addition, a comprehensive general health blood test (including determination of a lipid profile, vitamin levels, and ~50 other biomarkers) was performed on the same set of donors at the same experimental timepoint. The automated cell classification method produced immune signatures for all donors. These signatures were then evaluated using linear regression models to detect significant changes in immune cell populations based on vitamin D level, with sex and age group (<30 years: young, >=30<60 years: middle, >=60 years old) as covariates. Following the application of multiple testing correction, a total of 60 immune populations were identified as affected by variations of Vitamin D level in both sexes and across age groups.

Recovering the significant interaction and trajectory of Vitamin D with Th2 cells, implicated in allergic responses (Georas, et al. (20005), "T-helper cell type-2 regulation in allergic disease", Eur Respir J. 26(6):1119-37), and Th17 cells, implicated in autoimmune diseases and infection response pathways, (Zambrano-Zaragoza, et al. (2014), "Th17 cells in autoimmune and infectious diseases", Int J Inflam. 2014:651503) provides a reference range for the baseline phenotype of these two crucial populations in a healthy cohort, which could be used as a monitoring and diagnostic metric for patients undergoing treatment for any of these conditions.

Figure 13A:
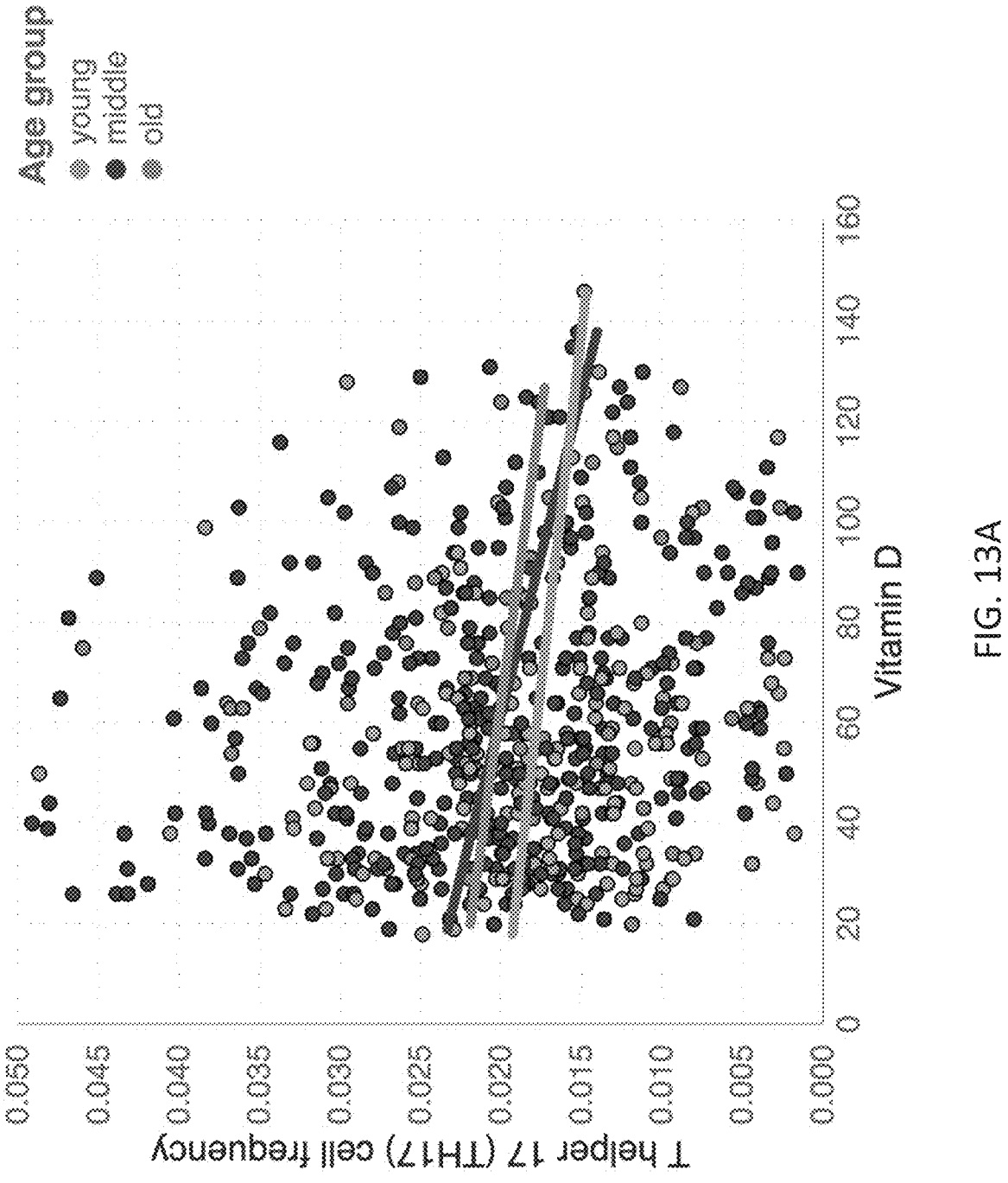
FIG. 13A provides a non-limiting example of data for T helper 17 (T17) cell frequency versus Vitamin D level for different age groups accounting for sex as a covariate.
Figure 13B:
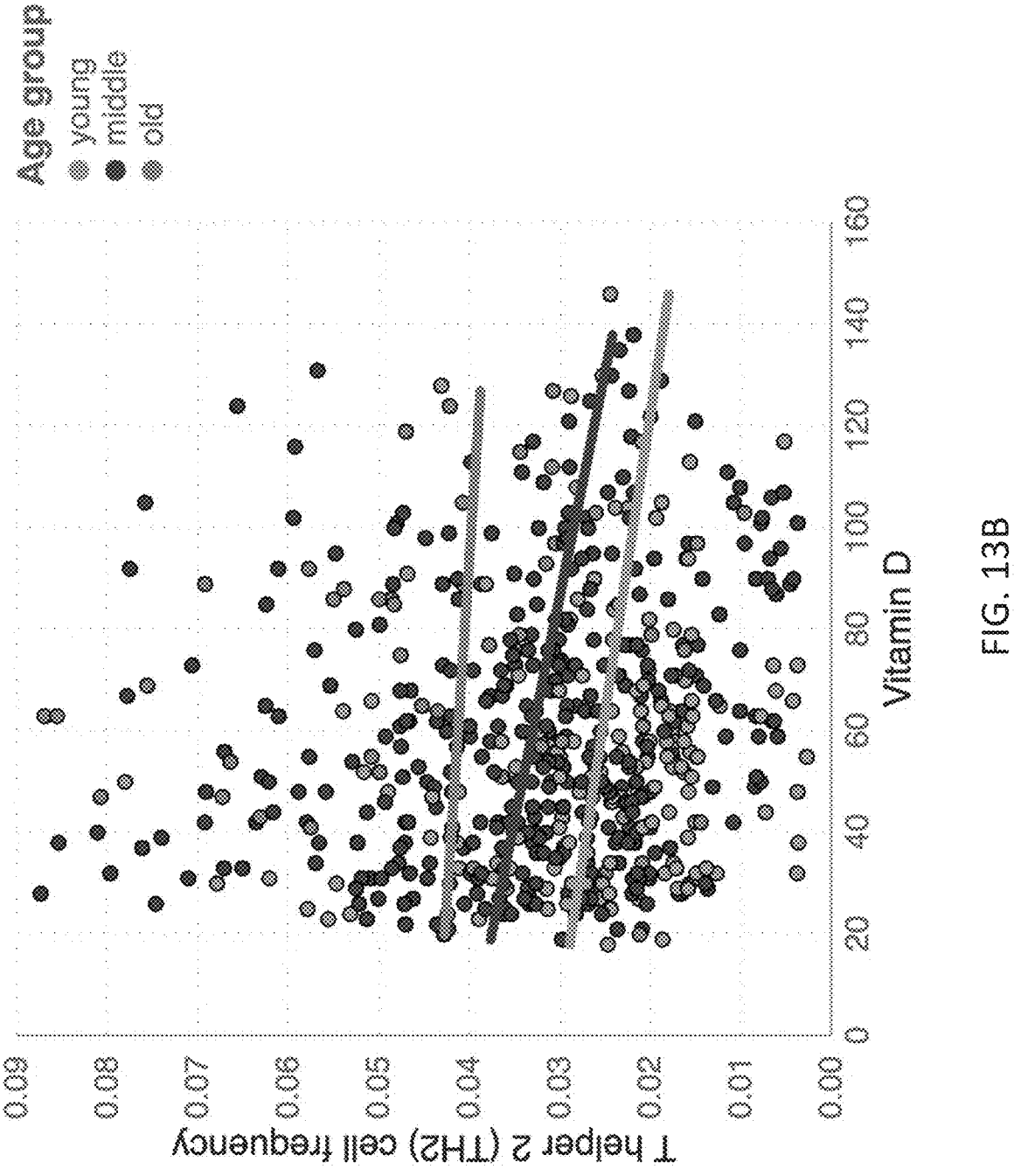
FIG. 13B provides a non-limiting example of data for T helper 2 (T2) cell frequency versus Vitamin D level for different age groups accounting for sex as a covariate.

FIGS. 13A-B provide non-limiting example plots showing the trajectory of T helper 2 (FIG. 13B) and T helper 17 (FIG. 13A) cell populations decreasing as Vitamin D levels increase in 609 health individuals across age groups accounting for sex as a covariate.

It should be understood from the foregoing that, while particular implementations of the disclosed methods and systems have been illustrated and described, various modifications can be made thereto and are contemplated herein. It is also not intended that the invention be limited by the specific examples provided within the specification. While the invention has been described with reference to the aforementioned specification, the descriptions and illustrations of the preferable embodiments herein are not meant to be construed in a limiting sense. Furthermore, it shall be understood that all aspects of the invention are not limited to the specific depictions, configurations or relative proportions set forth herein which depend upon a variety of conditions and variables. Various modifications in form and detail of the embodiments of the invention will be apparent to a person skilled in the art. It is therefore contemplated that the invention shall also cover any such modifications, variations and equivalents.

What is claimed is:
1. A method for generating an immune profile for a subject, the method comprising:
   contacting at least a first aliquot of a sample from the subject with at least a first immunophenotyping panel to fluorescently-label cells contained within the sample;

processing the fluorescently-labeled cells using a full spectrum flow cytometer to generate fluorescence intensity data, or data derived therefrom, for a plurality of fluorescently-labeled cells from the sample;
   providing at least a subset of the fluorescence intensity data, or data derived therefrom, for the plurality of fluorescently-labeled cells as input to an ensemble machine learning model configured to process the fluorescence intensity data, or data derived therefrom, and classify individual cells of the plurality of fluorescently-labeled cells as belonging to one of a plurality of distinct immune cell sub-populations; and
   outputting a total cell count or cell frequency for each of the plurality of distinct immune cell sub-populations in the sample as part of an immune profile for the subject.

2. The method of claim 1, wherein the ensemble machine learning model is organized in a cascading hierarchical tree structure comprising a plurality of nodes, and wherein each node comprises an individual machine learning model.

3. The method of claim 2, wherein each individual machine learning model comprises one input data set and from one to eight output data sets corresponding to branches of the cascading hierarchical tree structure.

4. The method of claim 2, wherein each individual machine learning model comprises a neural network model or a gradient descent boosted tree model.

5. The method of claim 2, wherein the plurality of nodes comprises at least 1000, 1200, 1400, 1600, 1800, 2000, 2200, or 2400 nodes.

6. The method of claim 2, wherein a number of individual machine learning models in the ensemble machine learning model is equal to a number of distinct immune cell sub-populations in the plurality of distinct immune cell sub-populations.

7. The method of claim 2, wherein the design of the cascading hierarchical tree structure is based at least in part on an expert analysis of manually-gated fluorescence intensity data, or data derived therefrom, for one or more control samples.

8. The method of claim 1, wherein individual cells are classified independently of all other cells in the plurality of fluorescently-labeled cells.

9. The method of claim 1, wherein individual cells are classified recursively with all other cells of the plurality of fluorescently-labeled cells.

10. The method of claim 1, wherein the ensemble machine learning model is trained using one or more labeled training data sets generated by an expert through manual gating of fluorescence intensity data, or data derived therefrom, for one or more control samples.

11. The method of claim 10, wherein the individual machine learning models in the ensemble machine learning model are trained individually using the one or more labeled training data sets.

12. The method of claim 10, wherein, during training, an individual model's predictions are used to validate the individual model but do not propagate forward through the ensemble machine learning model, thereby eliminating error propagation during training.

13. The method of claim 10, wherein the individual machine learning models in the ensemble machine learning model are trained collectively using a recursive training method.

14. The method of claim 10, wherein the training of the ensemble machine learning model is controlled by one or more hyperparameter values that are the same for every node in the cascading hierarchical tree structure.

15. The method of claim 10, wherein the training of the ensemble machine learning model is controlled by one or more hyperparameter values that are different for a subset of nodes in the cascading hierarchical tree structure.

16. The method of claim 10, wherein the training of the ensemble machine learning model is controlled by one or more hyperparameter values that are determined by performing a random grid search of the value ranges for the one or more hyperparameters.

17. The method of claim 1, further comprising performing a mathematical transformation of the fluorescence intensity data, or data derived therefrom, prior to using the transformed fluorescence intensity data as input for the ensemble machine learning model.

18. The method of claim 1, wherein the fluorescence intensity data, or data derived therefrom, comprises fluorescence intensity data for at least 2, 3, 4, 5, 6, 7, 8, 9, 10, 11, 12, 13, 14, 15, 20, 25, 30, 35, or 40 fluorescence detection channels.

19. The method of claim 18, wherein the fluorescence intensity data, or data derived therefrom, further comprises forward scatter height data, forward scatter area data, side scatter height data, side scatter area data, autofluorescence data, or any combination thereof.

20. The method of claim 1, wherein the sample comprises a blood sample, a buffy coat sample, or a cell suspension.

21. The method of claim 1, wherein the at least one immunophenotyping panel comprises a panel of fluorescently-labeled antibodies directed to cell surface proteins associated with antigen-presenting cells (APCs).

22. The method of claim 21, wherein the panel of fluorescently-labeled antibodies further comprises fluorescently-labeled antibodies directed to cell surface markers that are indicative of live cells, dead cells, or both.

23. The method of claim 1, wherein the at least one immunophenotyping panel comprises a panel of fluorescently-labeled antibodies directed to cell surface proteins associated with T cells.

24. The method of claim 1, wherein the plurality of distinct immune cell sub-populations comprises at least 1000, 1200, 1400, 1600, 1800, 2000, 2200, or 2400 distinct immune cell sub-populations.

25. The method of claim 1, wherein the plurality of distinct immune cell sub-populations includes white blood cells (WBC), Eosinophils, Eosinophil/CD5+, Neutrophils, Neutrophils/big, Neutrophils/CD5+, Neutrophils/small, B-cells, B-cells/CD5− CD27−, Monocytes/CD56+, Monocytes/CD56−, NK-cells, Dendritic cells (DC), T-cells, iNKT cells, gamma delta T-cells (total GD), Vd1 cells, Vd2 cells, Vdx cells, Mucosal-associated invariant T (MAIT) cells, TEMRA cells, CD4 naïve cells, T helper cells, CD4 effector memory cells, Treg cells, or any combination thereof.

26. The method of claim 1, wherein the total cell count or cell frequency for each of the plurality of distinct immune cell sub-populations in the sample is output as part of an immune profile in less than 24 hours, 12 hours, 10 hours, 8 hours, 6 hours, or 4 hours.

27. The method of claim 1, wherein the immune profile is used to diagnose an immune-related disease or disorder, monitor progression of an immune-related disease or disorder, or monitor a response to treatment of an immune-related disease or disorder in the subject.

28. A computer-implemented method for generating an immune profile for a subject, the method comprising:

receiving fluorescence intensity data, or data derived therefrom, generated using a full spectrum flow cytometer to process a fluorescently-labeled cell sample collected from the subject;

providing at least a subset of the fluorescence intensity data, or data derived therefrom, for a plurality of fluorescently-labeled cells as input to an ensemble machine learning model configured to process the fluorescence intensity data, or data derived therefrom, and classify individual cells of the plurality of fluorescently-labeled cells as belonging to one of a plurality of distinct immune cell sub-populations; and outputting a total cell count or cell frequency for each of the plurality of distinct immune cell sub-populations in the sample as part of an immune profile for the subject.

29. A system comprising:

one or more processors; and a memory communicatively coupled to the one or more processors and configured to store instructions that, when executed by the one or more processors, cause the system to:

receive fluorescence intensity data, or data derived therefrom, generated using a full spectrum flow cytometer to process a fluorescently-labeled cell sample collected from a subject;

provide at least a subset of the fluorescence intensity data, or data derived therefrom, for a plurality of fluorescently-labeled cells as input to an ensemble machine learning model configured to process the fluorescence intensity data, or data derived therefrom, and classify individual cells of the plurality of fluorescently-labeled cells as belonging to one of a plurality of distinct immune cell sub-populations; and output a total cell count or cell frequency for each of the plurality of distinct immune cell sub-populations in the sample as part of an immune profile for the subject.

30. The system of claim 29, wherein the system further comprises a full spectrum flow cytometer.

* * * * *